(12) United States Patent
Lewis et al.

(10) Patent No.: US 12,724,025 B2
(45) Date of Patent: Sep. 1, 2026

(54) METHOD FOR DETECTING URINARY TRACT INFECTIONS AND SAMPLE ANALYSIS USING LIQUID CHROMATOGRAPHY

(71) Applicants: Ian Andrew Lewis, Calgary (CA); Daniel Gregson, Calgary (CA); Ryan Groves, Calgary (CA)

(72) Inventors: Ian Andrew Lewis, Calgary (CA); Daniel Gregson, Calgary (CA); Ryan Groves, Calgary (CA)

( * ) Notice: Subject to any disclaimer, the term of this patent is extended or adjusted under 35 U.S.C. 154(b) by 892 days.

(21) Appl. No.: 15/734,163

(22) PCT Filed: May 31, 2019

(86) PCT No.: PCT/CA2019/050763
§ 371 (c)(1),
(2) Date: Dec. 1, 2020

(87) PCT Pub. No.: WO2019/227235
PCT Pub. Date: Dec. 5, 2019

(65) Prior Publication Data

US 2021/0215668 A1 Jul. 15, 2021

Related U.S. Application Data

(60) Provisional application No. 62/679,565, filed on Jun. 1, 2018.

(51) Int. Cl.
*G01N 33/493* (2006.01)
*G01N 30/72* (2006.01)
*G01N 30/46* (2006.01)

(52) U.S. Cl.
CPC .......... *G01N 33/493* (2013.01); *G01N 30/72* (2013.01); *G01N 30/466* (2013.01); *G01N 2800/348* (2013.01)

(58) Field of Classification Search
CPC .......... G01N 33/493; G01N 2800/348; G01N 30/72; G01N 30/466
See application file for complete search history.

(56) References Cited

U.S. PATENT DOCUMENTS 6,942,793 B2 9/2005 Ito et al.
2011/0151497 A1* 6/2011 Chinnaiyan ...... G01N 33/57434 436/64

(Continued)

FOREIGN PATENT DOCUMENTS

CN 106604707 A 4/2017
WO 2013/130875 A1 9/2013

OTHER PUBLICATIONS

Alteri et al. "Fitness of *Escherichia coli* during Urinary Tract Infection Requires Gluconeogenesis and the TCA Cycle", May 29, 2009, PLOS Pathogens, vol. 5(5): e1000448, p. 1-13. (Year: 2009).*

(Continued)

*Primary Examiner* — Samira J Jean-Louis
*Assistant Examiner* — Amelia Nicole Dickens
(74) *Attorney, Agent, or Firm* — McDonnell Boehnen Hulbert & Berghoff LLP

(57) ABSTRACT

Methods for analyzing a urine sample to determine if it contains a microorganism linked to an infection. The method comprising: providing culture-independent urine sample from patient; and analyzing the sample; where the culture-independent urine sample contains a microorganism linked to a UTI if at least one decarboxylated amino acid metabolite selected from agmatine, putrescine or cadaverine is detected in the culture-independent urine sample. The presence of agmatine is strongly indicative of a urinary tract infection caused by a majority of UTI-causing microorganisms. Another method for sample analysis, for or apart from UTI issues, employs liquid chromatography and mass spectroscopy of eluents separated using continuous chromatography (Continued)

of a sample spiked with an amount of isotopically labelled target compound. In another embodiment, the method further employs two-stage, isocratic continuous chromatography and possibly including chromatography through more than one column with elution to a common mass spectrometer.

5 Claims, 14 Drawing Sheets

(56) References Cited

U.S. PATENT DOCUMENTS

2016/0333388 A1 11/2016 Kostrzewa et al.
2017/0285006 A1 10/2017 Danell

OTHER PUBLICATIONS

Boudonck et al. "Discovery of Metabolomics Biomarkers for Early Detection of Nephrotoxicity", 2009, Toxicologic Pathology, vol. 37, p. 280-292 (Year: 2009).*
Chiles et al. "Fast LC-MS Quantitation of Glucose and Glycerol Via Enzymatic Derivatization", Available online Mar. 30, 2019, Analytical Biochemistry, vol. 575, p. 40-43. (Year: 2019).*
Robards et al. "5—High-performance Liquid Chromatography—Instrumentation and Techniques", 2004, Principles and Practice of Modern Chromatographic Methods, pp. 227-303. (Year: 2004).*
Srinivasan et al. "Metabolic Signatures of Bacterial Vaginosis", Apr. 14, 2015, mBio, vol. 6 Issue 2, e00204-15, p. 1-16. (Year: 2015).*
Armbruster et al. "Arginine promotes Proteus mirabilis motility and fitness by contributing to conservation of the proton gradient and proton motive force", Oct. 2014, Microbiology Open, vol. 3 Issue 5, p. 630-641. (Year: 2014).*
Ciccimaro and Blair, "Stable-Isotope Dilution LC-MS for Quantitative Biomarker Analysis", Feb. 9, 2010, Bioanalysis, vol. 2 Issue 2, p. 311-341. (Year: 2010).*
Satink et al. "Microbial influences on urinary polyamine excretion", Feb. 22, 1989, Clinica Chimica Acta, vol. 179, Issue 3, pp. 305-314. (Year: 1989).*
Stickle et al. "Quantitation of the Putative Neurotransmitter Agmatine as the Hexafluoroacetylacetonate Derivative by Stable Isotope Dilution Gas Chromatography and Negative-Ion Chemical Ionization Mass Spectrometry", Jul. 1, 1996, Analytical Biochemistry, vol. 238, Issue 2, pp. 129-136. (Year: 1996).*
Liu et al. "Determination of polyamine metabolome in plasma and urine by ultrahigh performance liquid chromatography-tandem mass spectrometry method: Application to identify potential markers for human hepatic cancer", Aug. 12, 2013, Analytica Chimica Acta, vol. 791, pp. 36-45 (Year: 2013).*
Yu et al. "Quantification of free polyamines and their metabolites in biofluids and liver tissue by UHPLC-MS/MS: application to identify the potential biomarkers of hepatocellular carcinoma", Jul. 3, 2015, Analytical and Bioanalytical Chemistry, vol. 407, pp. 6891-6897. (Year: 2015).*
Zhao et al. "Determination of agmatine in biological samples by capillary electrophoresis with optical fiber light-emitting-diode-induced fluorescence detection", Aug. 4, 2006, Journal of Chromatography A, vol. 1123, Issue 1, pp. 138-141 (Year: 2006).*
Zhao et al. "Quantification of biogenic amines by microchip electrophoresis with chemiluminescence detection", Jun. 26, 2009, Journal of Chromatography A, vol. 1216, Issue 26, pp. 5155-5159 (Year: 2009).*
Extended European Search Report dated Feb. 7, 2022 for European Application No. 19811477.9, 10 pages.
Hakkinen et al., "Analysis of free, mono- and dacetylated polyamines from human urine by LC-MS/MS", Journal of Chromatography B, 941 (2013) 81-89.
Niemi, MD et al., "Urinary Polyamines as Biomarkers for Ovarian Cancer", International Journal of Gynecological Cancer, vol. 27, No. 27, No. 7, Sep. 2017, 7 pages.
Pacchiarotta et al., "Fibrinogen alpha chain O-glycopeptides as possible markers of urinary tract infection", Journal of Proteomics, 75 (2012) 1067-1073.
English Translation of first Office Action for Chinese Patent Application No. 201980047248.4 dated Jan. 30, 2024, pp. 1-11.
Fu, Shanji et al. Determination of polyamines in human prostate by high-performance liquid chromatography with fluorescence detection Journal of Chromatography B 709 (1998), pp. 297-300.
Antti et al. "Metabolic Profiling for Detection of *Staphylococcus aureus* Infection and Antibiotic Resistance", PLoS One, 2013, 8(2), e56971, 1-11.
Palama et al. "Identification of bacterial species by untargeted NMR spectroscopy of the exo-metabolome", Analyst, 2016, 141(15), 4558-61.
The International Search Report (ISR) with Written Opinion for PCT/CA2018/050301 dated Jun. 8, 2018, pp. 1-9.
Satink et al., "Microbial influences on urinary polyamine excretion", Clinica Chimica Acta, 1989, vol. 179, 305-314.
Bower et al., "Polyamine-Mediated Resistance of Uropathogenic Escherichia coli to Nitrosative Stress", Journal of Bacteriology, 2006, 188(3), 928-933.
Byun et al., "Analysis of polyamines as carbamoyl derivatives in urine and serum by liquid chromatography-tandem mass spectrometry", Biomedical Chromatography, 2008 (published online Jul. 31, 2007), vol. 22, 73-80.
Gika et al., "Quantitative profiling of polar primary metabolites using hydrophilic interaction ultrahigh performance liquid chromatography-tandem mass spectrometry", Journal of Chromatography A, 2012, vol. 1259, 121-127.
Taibi et al., "Rapid and simultaneous high-performance liquid chromatography assay of polyamines and monoacetylpolyamines in biological specimens", Journal of Chromatography B, 2000, vol. 745, 431-437.
Van Pelt et al., "A Four-Column Parallel Chromatography System for Isocratic or Gradient LC/MS Analyses", Anal. Chem., 2001, 73(3), 582-588.
Abe et al., "Determination of Polyamines in Human Urine by High-Performance Liquid Chromatography with Fluorescence Detection", Jap. J. Clin. Chem., 1985, 14(5), 315-320.
Alteri et al., "Fitness of *Escherichia coli* during Urinary Tract Infection Requires Gluconeogenesis and the TCA Cycle", PLoS Pathogens, 2009, 5(5), e1000448, 1-13.
The International Search Report (ISR) with Written Opinion for PCT/CA2019/050763 dated May 31, 2019, pp. 1-15.
Revermann, et al., "Quantitative analysis by microchip capillary electrophoresis—current limitations and problem-solving strategies," Analyst, vol. 133, pp. 167-174, 2008.
Schaeper, J.P., "Reproducibility and optimization in capillary electrophoresis," PhD diss., University of Tennessee, 2002.

* cited by examiner

Lower limit of detection
50 nM

Lower limit of quantification
100 nM

Dynamic range
> 100 fold

METHOD FOR DETECTING URINARY TRACT INFECTIONS AND SAMPLE ANALYSIS USING LIQUID CHROMATOGRAPHY

CROSS-REFERENCE TO RELATED APPLICATIONS

This application is a U.S. national phase of International Application No. PCT/CA2019/050763, filed May 31, 2019, which claims priority from U.S. Provisional Application No. 62/679,565, filed Jun. 1, 2018, the disclosure of each of which is hereby incorporated by reference in its entirety.

FIELD

This invention relates to methods for detecting urinary tract infections (UTIs). The invention also relates to clinical sample analysis using liquid chromatography.

BACKGROUND

More than 75% of urinary tract infections (UTIs) are caused by organisms from the Enterobacteriaceae family including one or more of the following microorganisms: *Escherichia coli* (EC); *Klebsiella* species such as *Klebsiella pneumoniae* (KP) or *Klebsiella oxytoca* (KO); *Proteus mirabillis* (PM); *Enterobacter* species (Esp); and *Citrobacter* species (Csp) (hereinafter common UTI-causing microorganisms).

Urinary tract infections (UTIs) are very common and affect over half of women during their lifetime. As a result, urine culture is one of the most common tests done in microbiology. Current UTI diagnostic procedures require bacterial culturing steps, which contribute to long diagnostic timelines. Using the current techniques, it takes approximately two days to identify a UTI-causing organism and characterize its antibiotic susceptibility profile.

Under ideal circumstances, the organism(s) causing a UTI would be identified and their antibiotic susceptibility would be measured before antibiotics were prescribed to ensure proper infection management. However, the long timelines required for UTI diagnosis make it impractical to wait for clinical results. Consequently, many patients are given antibiotic therapy that is not properly matched to their condition. A faster diagnostic method would reduce complications from improperly treated UTIs.

SUMMARY OF THE INVENTION

Methods have been invented for detecting urinary tract infections (UTI).

A method has been invented for analyzing a urine sample to determine if it contains a microorganism linked to a urinary tract infection. A urine sample can be analyzed to determine if it contains at least one decarboxylated amino acid metabolite selected from agmatine, putrescine or cadaverine. The presence of agmatine, putrescine or cadaverine in urine is indicative of a urinary tract infection caused by any of the common UTI-causing microorganisms. The presence of agmatine is strongly indicative of a urinary tract infection caused by any of the common UTI-causing microorganisms.

Thus, in accordance with an aspect of the present invention, there is provided a method of diagnosing a urinary tract infection (UTI) in a patient, the method comprising: receiving a culture-independent urine sample from the patient; analyzing the culture-independent urine sample; and wherein the patient is diagnosed as having the UTI if at least one of agmatine, putrescine or cadaverine is detected in the culture-independent urine sample.

In accordance with another broad aspect of the present invention, there is provided an antibiotic for the use in therapy of a patient that is suffering from a UTI associated with the presence of at least one of agmatine, putrescine or cadaverine is detected in the culture-independent urine sample; wherein the antibiotic is selected to be active against an Enterobacteriaceae species; and wherein the at least one of agmatine, putrescine or cadaverine is detected in the patient's culture-independent urine sample.

In accordance with another broad aspect of the present invention, there is provided a use of an antibiotic for treatment of a patient that is suffering from a UTI associated with the presence of at least one of agmatine, putrescine or cadaverine in the patient's culture-independent urine sample; wherein the antibiotic is selected to be active against an Enterobacteriaceae species; and wherein the metabolite is detected in patient's culture-independent urine sample.

While urine samples can be analyzed by various methods for at least one of agmatine, putrescine or cadaverine, a method for rapid sample analysis is of great value since a laboratory may have many hundreds of samples to analyze every day due to the frequency of UTIs. Thus, a method for sample analysis, for or apart from UTI issues, has also been invented. The method offers rapid analysis of complex samples such as body fluids for example urine samples in the case of UTIs and blood samples in the case of blood stream infections. The method employs liquid chromatography and mass spectroscopy analysis of chemical substances, in which samples are injected into the liquid chromatography system in a consecutive series of sample plugs under conditions where the target substance(s) will elute under isocratic continuous conditions. In another embodiment, the method employs a multistage isocratic continuous elution, with continuous, serial injections in one stage and rapid elution from the column in a second stage.

Thus, in accordance with other aspects of the present invention, there is provided a method for rapid sample analysis of a plurality of samples for the presence of a target compound, the method comprising: injecting continuously a plurality of samples, one at a time and in series, onto a LC column with an isocratic solvent, the isocratic solvent providing substantially gradual elution of the target compound; and receiving the one or more analytes to a mass spectrometer for analyte detection to determine if the one or more analytes includes the target compound.

In accordance with another broad aspect of the present invention, there is provided a LC-MS apparatus for rapid sample analysis for detection of a target compound, the apparatus comprising: a first column configured for liquid chromatography; a second column configured for liquid chromatography and in parallel to the first column; a detector for detecting compounds, including the target compound, which are eluted from the first column and second column; a sample injector for injecting a plurality of samples in series alternating onto the first column and the second column along with a first mobile phase; a solvent pump for injecting a second mobile phase different that the first mobile phase alternating on the first column and the second column; and a valve switch for alternating communication of the sample injector and the solvent pump to the first column and the second column.

In accordance with another broad aspect of the present invention, there is provided a LC-MS apparatus for rapid sample analysis providing serial elution of a plurality of culture-independent samples for detection of a target compound, the apparatus comprising: a LC column; a first mobile phase for injecting samples onto the LC column; a second mobile phase, having a different composition than the first mobile phase configured to elute samples off the LC column; a detector for detecting compounds, including the target compound, which are eluted from the LC column; a sample injector configured to inject the plurality of culture-independent samples in series onto the LC column; and a valve switch to switch between the first mobile phase and the second mobile phase; wherein the valve switch is configured to switch from the first mobile phase to the second mobile phase, after the plurality of samples are injected onto the LC column and the valve switch is configured switch from the second mobile phase to the first mobile phase, after the plurality of samples are eluted off the LC column.

In accordance with another broad aspect of the present invention, there is provided a method for analyzing a body fluid sample to determine if it contains a microorganism linked to an infection, the method comprising: providing body fluid sample from a patient; analyzing the sample on a liquid chromatography mass spectrometry (LC-MS) apparatus, where the sample is analyzed by the LC-MC apparatus and the liquid chromatography (LC) is run with an isocratic solvent; and wherein the body fluid sample contains a microorganism linked to an infection if a metabolite from the microorganism is detected in the body fluid sample by isocratic continuous LC-MS.

In one embodiment, a known amount of isotopically labeled substance, such as a decarboxylated amino acid, is added to a complex sample to enable quantification of target substance(s) by measuring an isotope ratio.

It is to be understood that other aspects of the present invention will become readily apparent to those skilled in the art from the following detailed description, wherein various embodiments of the invention are shown and described by way of example. As will be realized, the invention is capable for other and different embodiments and several details of its design and implementation are capable of modification in various other respects, all captured by the present claims. Accordingly, the detailed description and examples are to be regarded as illustrative in nature and not as restrictive.

DESCRIPTION OF THE FIGURES

For a better appreciation of the invention, the following Figures are appended.

DETAILED DESCRIPTION

Figure 1:
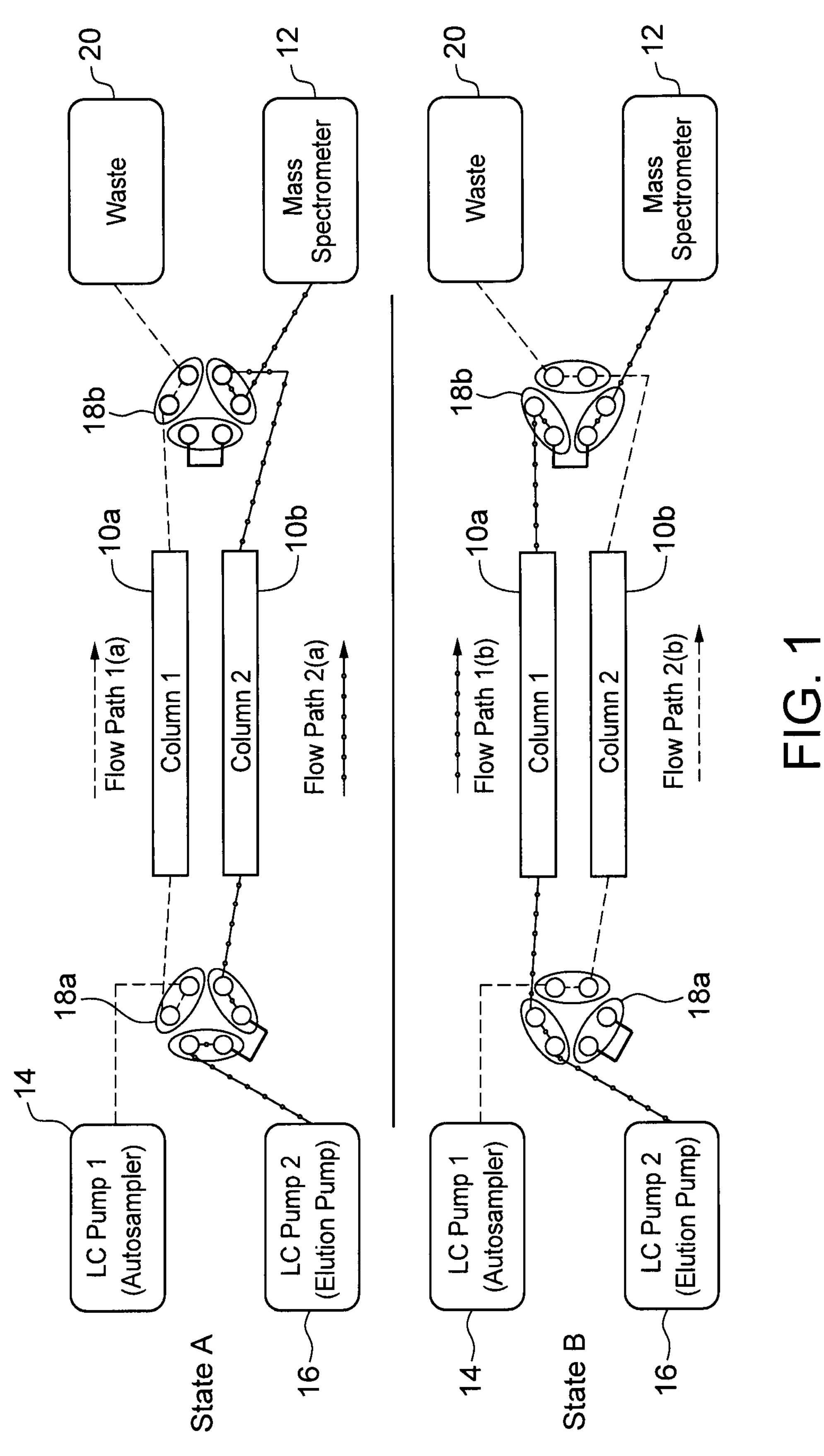
FIG. 1 is a schematic diagram of the two-stage isocratic continuous chromatography set up with a multiplexed column injection schedule where two columns were employed.

The detailed description and examples set forth below are intended as a description of various embodiments of the present invention and are not intended to represent the only embodiments contemplated by the inventor. The detailed description includes specific details for the purpose of providing a comprehensive understanding of the present invention. However, it will be apparent to those skilled in the art that the present invention may be practiced without these specific details.

Analysis of urine samples from humans indicated that surprisingly agmatine, putrescine or cadaverine were present in the urine samples at elevated levels in at least 75% of urinary tract infections (UTI) while this was not true of urine samples from healthy patients. The study showed that urine from human subjects without a UTI had agmatine, putrescine or cadaverine concentrations that were not detectable given the detection limits of the assay (50 nM).

As will be appreciated, analogues of metabolites, such as adducts, isotopomers, fragments, multiple charge states, etc., are also considered to be the metabolite. It is noted that a metabolite signal in spectrometric analysis may be complex and in fact may include more than one signal per molecule. Overall, the group of signals for that molecule can be resolved and considered a single metabolite signal. For example, a mass spectrometer will detect 10-50 signals for each molecule including the original molecule (parent) plus a variety of analogues of the original molecule including fragments, adducts (chemical combinations that happen in the instrument), multiple charge states and isotopomers (naturally occurring forms of the molecule with 1 or more extra neutrons). Detecting any of these signals can indicate one molecule, and in this application, any of the analogues of agmatine, putrescine or cadaverine are encompassed as the metabolite of interest: agmatine, putrescine or cadaverine.

The present research surprisingly concluded that UTI's caused by microbes of the Enterobacteriaceae family can be diagnosed by detecting agmatine, putrescine and/or cadaverine in the urine of a patient. The Enterobacteriaceae family of microbes includes *Escherichia coli, Proteus mirabilis, Citrobacter* species including *Citrobacter braakii, Citrobacter freundii, Citrobacter amalonaticus, Citrobacter farmeri* and *Citrobacter koseri, Enterobacter* species including *Enterobacter aerogenes* (now classified as *Klebsiella aerogenes*) and *Enterobacter cloacae* cplx., *Klebsiella* species including *Klebsiella oxytoca* and or *Klebsiella pneumoniae*. All Enterobacteriaceae studied produced agmatine, putrescine and/or cadaverine. Thus, regardless of whether the infection was from *Escherichia coli; Klebsiella* species; *Proteus mirabilis; Enterobacter* species; *Citrobacter* species, the infection can be identified by analyzing the patient's urine sample for a concentration of one or more of agmatine, putrescine or cadaverine. A threshold of 170 nM agmatine or greater in the urine is indicative of an Enterobacteriaceae infection.

Figure 9:
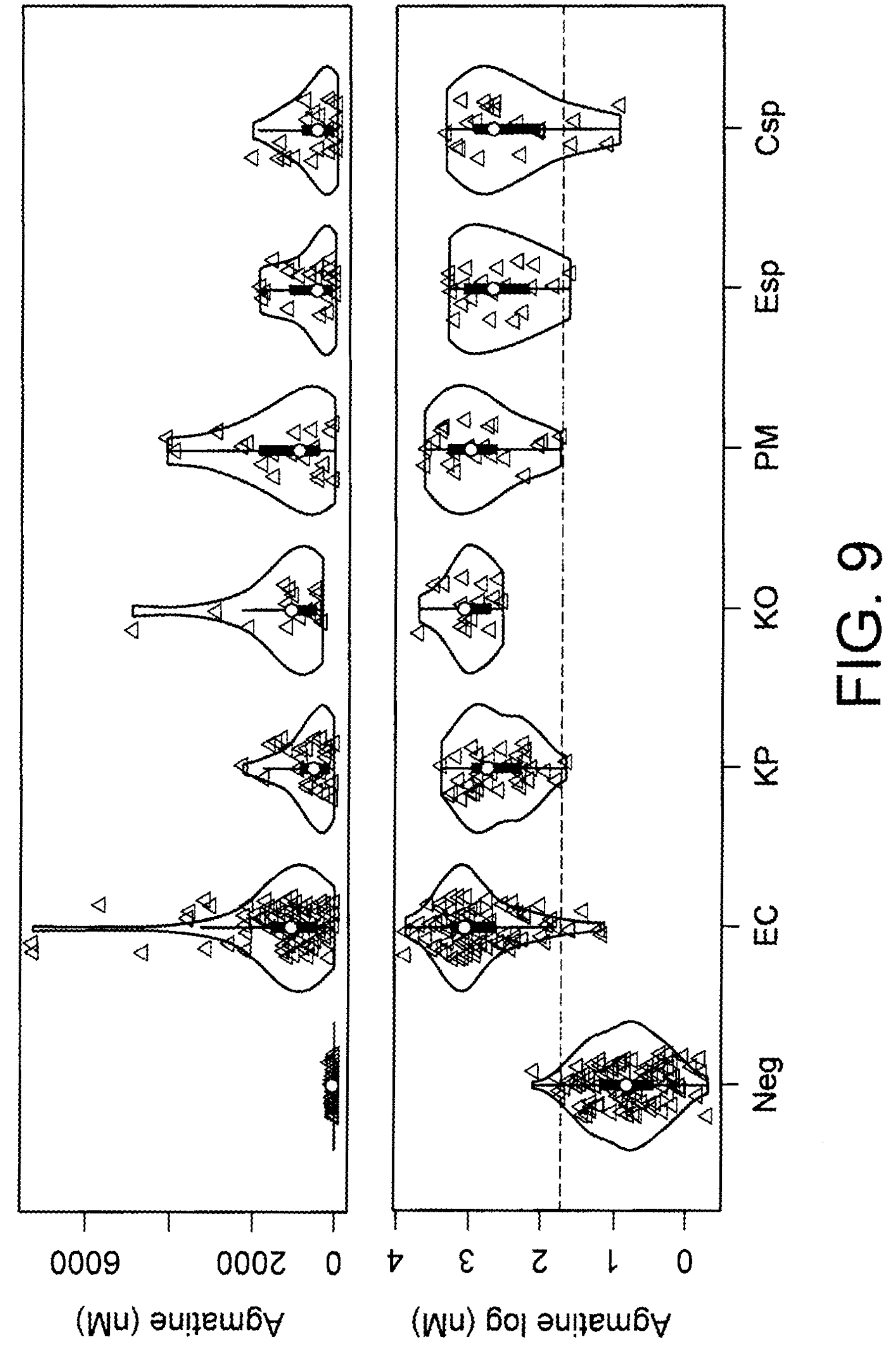
FIG. 9 is a plot showing agmatine concentrations observed in urine samples from healthy patients (Neg) and patients with urinary tract infections caused by six different types of bacteria—*Escherichia coli* (EC); *Klebsiella* species such as *Klebsiella pneumoniae* (KP) or *Klebsiella oxytoca* (KO); *Proteus mirabillis* (PM); *Enterobacter* species (Esp); and *Citrobacter* species (Csp). The upper block represents agmatine concentrations observed in the sample while the lower block shows the same data on a log 10 scale. Dotted lines in the second block indicate a threshold at 58 nM, which was determined by isotope ratio and corresponds to UTI detection threshold associated with a sensitivity of 0.94 and specificity of 0.99.
Figure 11:
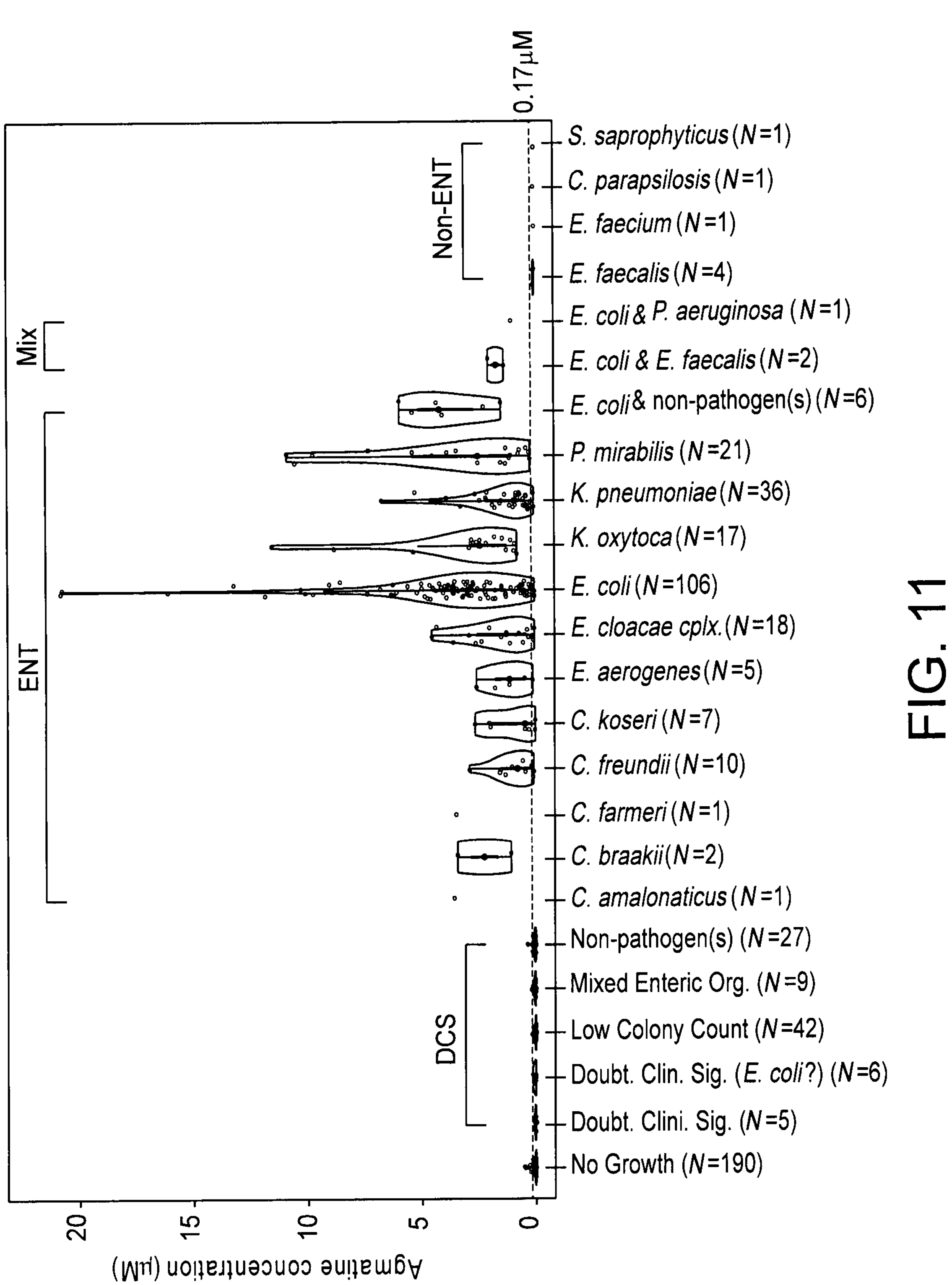
FIG. 11 is a schematic showing agmatine may be used as an indicator for the presence of a UTI. Five hundred and nineteen samples were obtained from Alberta Public Laboratories and analyzed. Agmatine concentrations were tightly linked to culture positive samples containing Enterobacteriaceae. The samples were split in the schematic into subgroups based on speciation results.

Agmatine was reliably identified in samples from patients suffering from an infection of at least one of *Escherichia coli, Proteus mirabilis, Citrobacter* species including *Citrobacter braakii, Citrobacter freundii, Citrobacter amalonaticus, Citrobacter farmeri and Citrobacter koseri, Enterobacter* species including *Enterobacter aerogenes* and *Enterobacter cloacae* cplx., *Klebsiella* species including *Klebsiella oxytoca* and *Klebsiella pneumoniae*. With reference to FIGS. 9 and 11, for example, urine samples from human subjects were analyzed and those samples from subjects infected with *Escherichia coli* (EC), *Proteus mirabilis* (PM), *Citrobacter* species (Csp) including *Citrobacter braakii, Citrobacter freundii, Citrobacter amalonaticus, Citrobacter farmeri* and *Citrobacter koseri, Enterobacter* species (Esp) including *Enterobacter aerogenes* and *Enterobacter cloacae* cplx., *Klebsiella* species including *Klebsiella oxytoca* (KO) and *Klebsiella pneumoniae* (KP) contained agmatine and those samples from subjects not suffering from any UTI (i.e. negative for UTI) had undetectable agmatine levels. Thus, surprisingly a test for agmatine in the urine can be employed to reliably indicate that a patient is suffering from an infection by any one of the common UTI-causing microorganisms. Putrescine (FIG. 6) and cadaverine can also be used as indicators, in some cases, to diagnose a UTI in a human subject.

Enterobacteriaceae such as *Escherichia coli, Proteus mirabilis, Citrobacter species, Enterobacter species*, and *Klebsiella* species produce agmatine, and sometimes putrescine or cadaverine, but the human body does not produce any of agmatine, putrescine or cadaverine in the urinary tract. Agmatine, putrescine and cadaverine are produced by the breakdown of protein, specifically amino acids. Agmatine is an aminoguanidine created by decarboxylation from the chemical arginine. Putrescine, or tetramethylenediamine, is a metabolite of ornithine or agmatine. Cadaverine is also known by the name pentamethylenediamine and is created by decarboxylation of the chemical lysine.

Thus, in one embodiment a method for determining if a patient has a urinary tract infection may include: analyzing a urine sample from the patient for the presence of agmatine, putrescine or cadaverine, a positive result indicating that the patient has a urinary tract infection resulting from at least one of *Escherichia coli; Klebsiella pneumoniae; Klebsiella oxytoca; Proteus mirabillis; Enterobacter* species; or *Citrobacter* species. Because the analysis detects a microorganism metabolite rather than a microorganism directly, sample handling is simplified, for example, the sample can be used without any culturing and, thus, the materials and the time required for culturing are avoided.

In one embodiment, the urine sample from the patient may be analyzed directly after collection. The sample may not need to be cultured and therefore a culture-independent sample may be used and a culture-independent analysis can be performed.

After collection, the urine sample may be tested immediately by this method. Alternatively, the human urine sample may be preserved using a preservative, for example a buffered borate solution, which prevents any microorganisms therein from growing. Alternatively, the urine sample, after collection may be fixed to stop microbial activity with a fixing agent, for example, methanol. Human urine sample preparation may also include removing solids, as by for example filtration or centrifuge. Thereafter, the liquid portion, for example the supernatant in the case of centrifugation, of the urine sample is analyzed for the presence of agmatine, putrescine or cadaverine.

Optionally, the sample can be enriched using solid phase extraction after fixing and solids removal. Solid phase extraction is used to purify biological samples. A stationary phase, for example, silica, along with a high pH mobile phase is used to capture molecules in the urine sample. The stationary phase then elutes molecules when the pH of the mobile phase is lowered, resulting in purification of the biological sample. A method for solid phase extraction is contained in Example 8.

Figure 10:
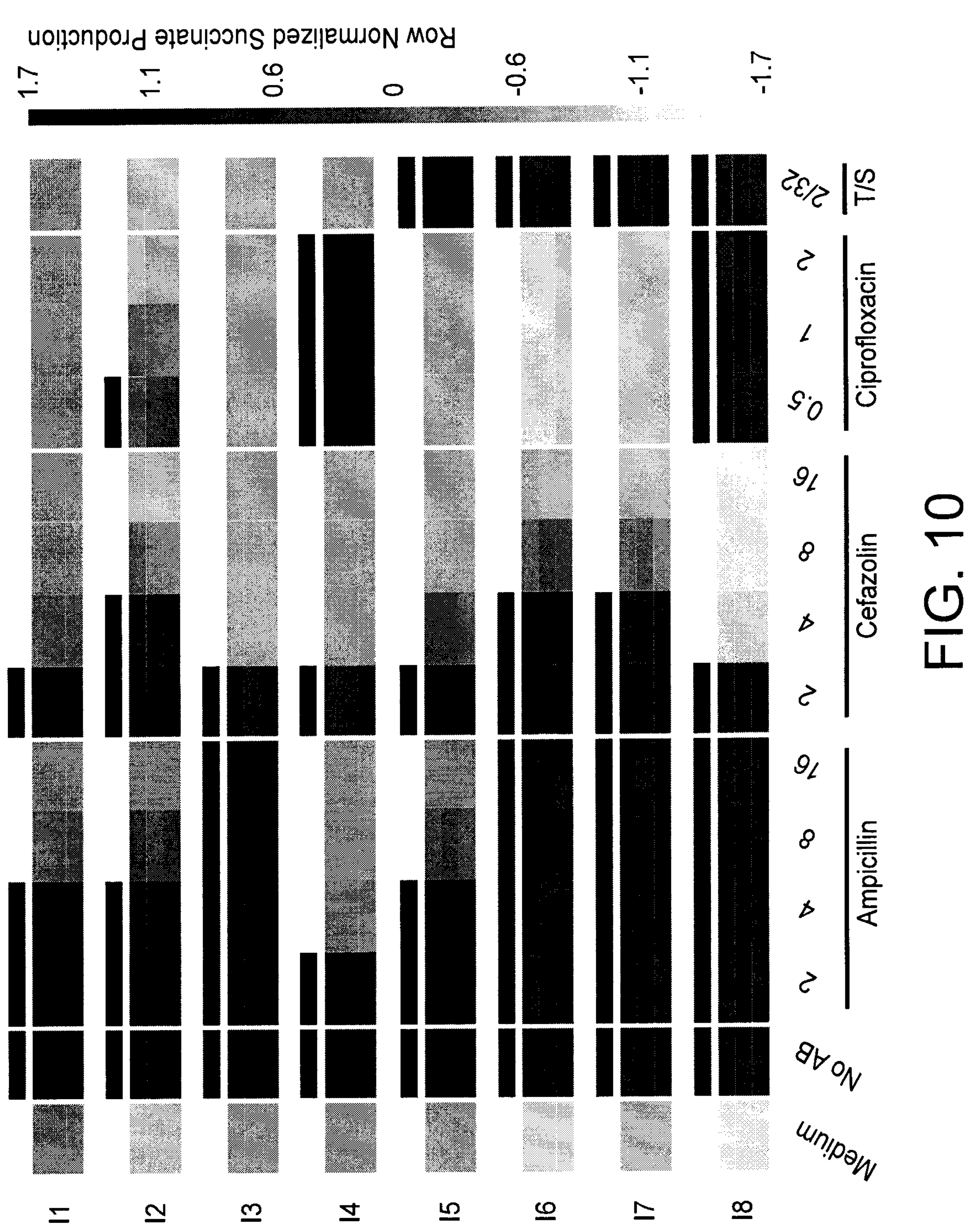
FIG. 10 is a schematic showing a metabolic preference assay (MPA) for determining the susceptibility of eight clinical *E. coli* isolates (rows I1-I8) to four antibiotics at a range of concentrations. Metabolic activity was monitored via succinate levels, a metabolite secreted by *Escherichia coli* in culture. Increased metabolite production relative to control medium (light grey) is indicative of metabolic activity characteristic of resistance to a given concentration of antibiotic. A decrease in metabolite production relative to control (dark grey) is indicative of antibiotic sensitivity. Three technical replicates were performed for each isolate, under each condition. Black bars are indicative of the antibiotic sensitivity profiles of each isolate, as determined by traditional culture based approach at a regional diagnostic laboratory (CLS). Concentrations are in μg/mL. Where T/S refers to trimethoprim-sulfamethoxazole.

If sample analysis gives a positive result for at least one of agmatine, putrescine or cadaverine, thereby indicating that the patient has a urinary tract infection, the sample can be further analyzed, if desired, to determine more about the cause of the UTI. For example, the urine sample can be tested for antibiotic resistance to determine the appropriate antibiotic that could be used to treat the UTI (FIG. 10). If the sample gives a positive result, a metabolic preference assay may be performed to determine the class of antibiotics that could be excluded from treatment of the UTI due to antibiotic resistance. The metabolic assay may also indicate the type of pathogen present, for example, gram negative or positive, genus, species etc. and, therefore, instead of a general antibiotic, a specific, appropriate course of antibiotic treatment may be administered to the patient.

The metabolic preference assay provides an identification of the cell type in a positive result sample, the assay including: incubating the sample in a growth medium; after incubation, analyzing the incubated growth medium by chemical analysis to determine a level of a metabolite in the incubated growth medium; and identifying the cell type by comparison of the level of the metabolite with reference metabolite profiles and matching the level of metabolite with a reference metabolite profile indicative of the cell type. The cell type of the organism may be the general class of the organism (i.e. gram negative, gram positive, etc.), the genus or species of origin (i.e. the bacterial species, etc.), or the strain or distinguishing characteristics (i.e. resistance or sensitivity to an antibiotic).

For a metabolic preference assay, the growth medium in which cells are grown provides nutrients and accumulates waste products, referred to as metabolites of the microorganism. The metabolic signal of microorganisms is amplified over time through cumulative changes in growth medium composition. The incubation period allows cells in the positive result sample to metabolize by consuming their preferred nutrient(s) and secreting waste products. Nutrients present in the medium are noted and metabolites after analysis are analyzed to obtain metabolic data for the organisms in the growth medium. Reference metabolite profiles, which are the known metabolite results for groups of microorganisms or individual species, subspecies or strains, are compared to the metabolic data acquired from analysis of the sample to classify the unknown organism. This method is described in more detail in WO 2018/165751, published Sep. 20, 2018 by the present applicant and incorporated herein by reference.

Due to the present rapid diagnosis, if agmatine, putrescine or cadaverine are detected in the urine sample, a more specific antibiotic can be administered to the patient such as ampicillin. Other possible treatments include ceptra, cephalosporins, nitrofurantoin, fosfomycin, and fluoroquinolones. However, rapid testing could reduce the need for broader spectrum agents such as fluoroquinolones or broad-spectrum cephalosporins. Above noted additional antibiotic sensitivity testing and/or metabolic preference assay, for the actual cell type within the Enterobacteriaceae family may permit a more refined and targeted selection of the antibiotic.

Analyzing a urine sample from the patient for the presence of agmatine, putrescine or cadaverine may be achieved by various technologies.

Spectrometric analysis technologies may be used. In some cases, sample separation such as by chromatographic separation may be employed ahead of spectrometric analysis.

In particular, detectors can be used to detect agmatine, putrescine or cadaverine in a urine sample from a patient. Useful detectors include a mass spectrometer, a UV-Vis spectrophotometric detector, arrayed diode detector, or nuclear magnetic resonance spectrometer.

These detectors may be employed to accept the sample after separation thereof or, sometimes directly. In particular, in some method, urine samples may be analyzed without separation such as chromatography, for example, using a direct injection strategy for example in combination with isotope dilution. This strategy is sometimes employed in cases where the target analyte has been purified from the urine sample or when ion suppression effects are controlled via isotope dilution. One current practice is to analyze samples via direct injection techniques that couple the auto sampler directly to a mass analyzer and thereby omit the chromatographic separation step. This direct injection strategy circumvents the time required for chromatographic approaches, but is only quantitatively robust when analyzing low-complexity solutions. Since diagnostic applications typically involve analyses of complex samples, current practices may include iterative sample extraction and molecular purification steps, such as Solid Phase Extraction (SPE). These procedures allow complex samples to be analyzed via rapid direct-injection approaches and minimize quantitative errors resulting from ion suppression, but introduce additional sources of experimental error.

Figure 2A:
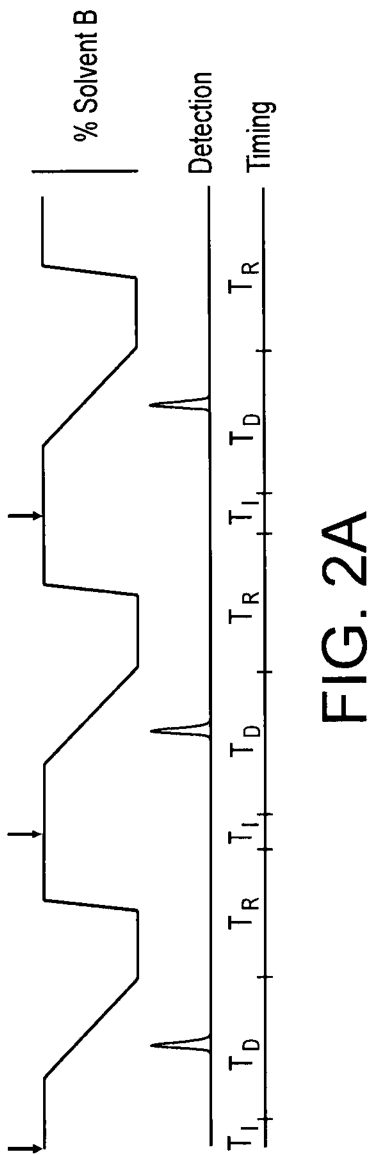
FIGS. 2A to 2D are schematic diagrams of the timing scenarios of LC analysis (TD) for multiple sample injections (TI) for four different chromatographic methods: a conventional 3 minute gradient (FIG. 2A); isocratic continuous chromatography (FIG. 2B); two stage isocratic continuous chromatography (FIG. 2C); and multiplexed, two stage isocratic continuous chromatography, where there are two columns each operating in a two-stage, isocratic continuous chromatographic method (FIG. 2D). The isocratic continuous chromatography (FIG. 2B) includes a time TI of repeated sample injections (arrows), followed by sample elute detection TD using an isocratic solvent and possibly followed by a column reconditioning TR using a selected mobile phase to clear the column. The two stage isocratic continuous chromatography (FIG. 2C) includes a first stage, including sample injection TI using Solvent B (i.e. a first mobile phase) and a second stage, including sample elution using a solvent different than solvent B (i.e. a second mobile phase) for during which the separated molecules elute as peaks and are detected TD, possibly followed by a column reconditioning stage TR using a selected mobile phase to clear the column. The multiplexed, two stage isocratic continuous chromatography (FIG. 2D) includes two columns, where when Column 1 is in the second stage TD and TR, Column 2 is in the first stage TI and the column stages alternate—such that more samples can be analyzed over time and more effective utilization of the detector can be achieved.

Most commonly, complex samples such as urine are analysed by separation first and then detection. Liquid chromatography (LC) is recognized as a useful approach for analyte separation from complex samples. Conventional liquid chromatography typically uses a gradient of two or more solvents, where after sample injection the type and concentration of solvent is varied over time, to separate the constituent compounds from each sample. Each sample is injected onto the column then eluted using a flow of solvent (the mobile phase), which varies in composition over time as shown in FIG. 2A. Although conventional chromatography is effective, the length of time required to inject a sample, complete a gradient, and allow the column to re-equilibrate is not ideal for analyses where a plurality of samples are to be analyzed in the minimum period of time. With conventional LC, it can be difficult to achieve robust data quality using LC run times shorter than 3 minutes when analyzing complex samples, such as urine (FIG. 3). While such time frames may be acceptable in some situations, the large number of clinical samples related to UTI that most clinics handle highlights the importance of sample throughput. Complex biological samples typically require extended LC gradients or multi-step extraction protocols to minimize quantitative problems related to ion suppression. However, time intensive methods are undesirable for clinical applications that routinely see hundreds of samples per day. Consequently, clinical LC must balance throughput with quantitative performance.

Figure 2B:
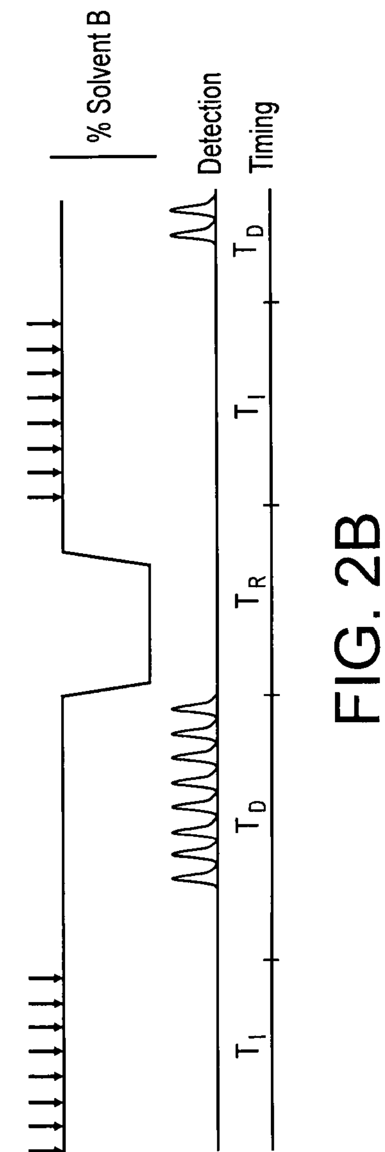
Figure 3A:
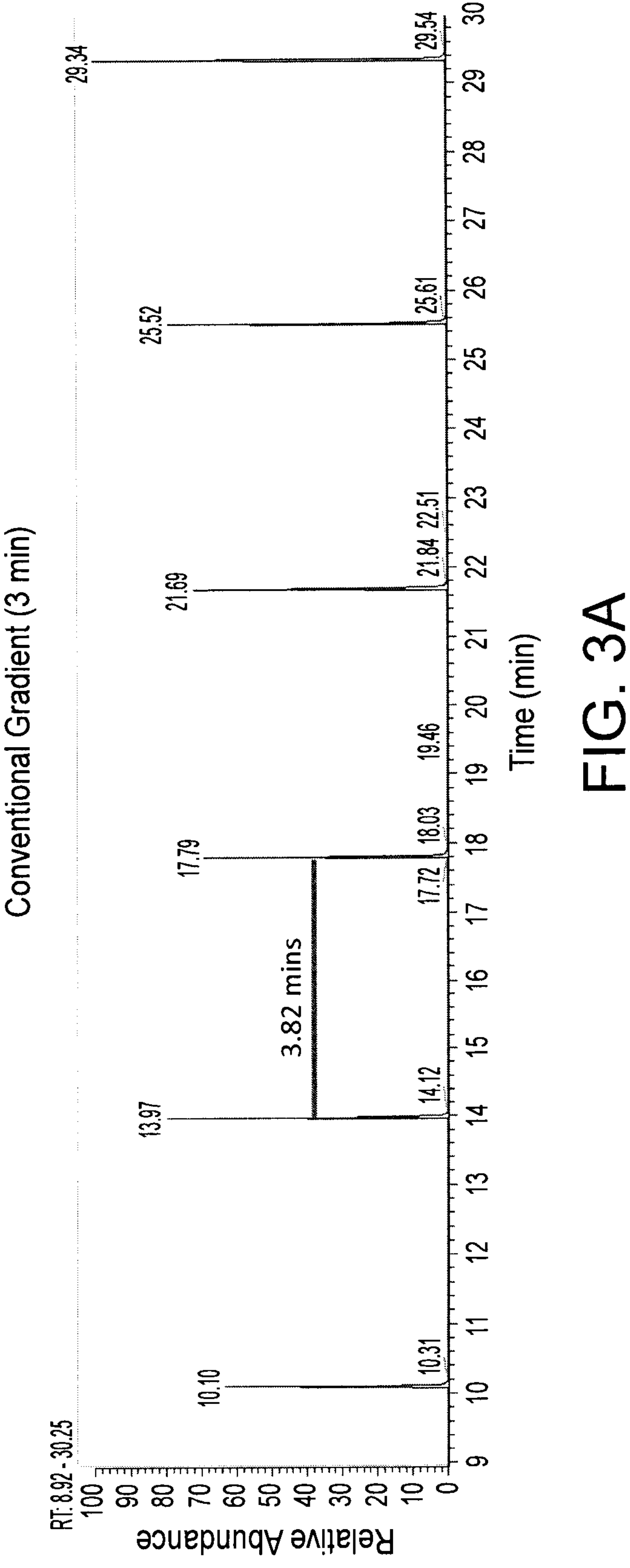
FIGS. 3A to 3C are comparisons of sample peaks eluted per laboratory unit time: from a conventional 3 minute gradient (FIG. 3A), isocratic continuous chromatography (FIG. 3B), and two-stage, isocratic continuous chromatography (FIG. 3C). The eluted samples arise from repeated injection of a sample of urine containing 5 uM of an agmatine standard.
Figure 3B:
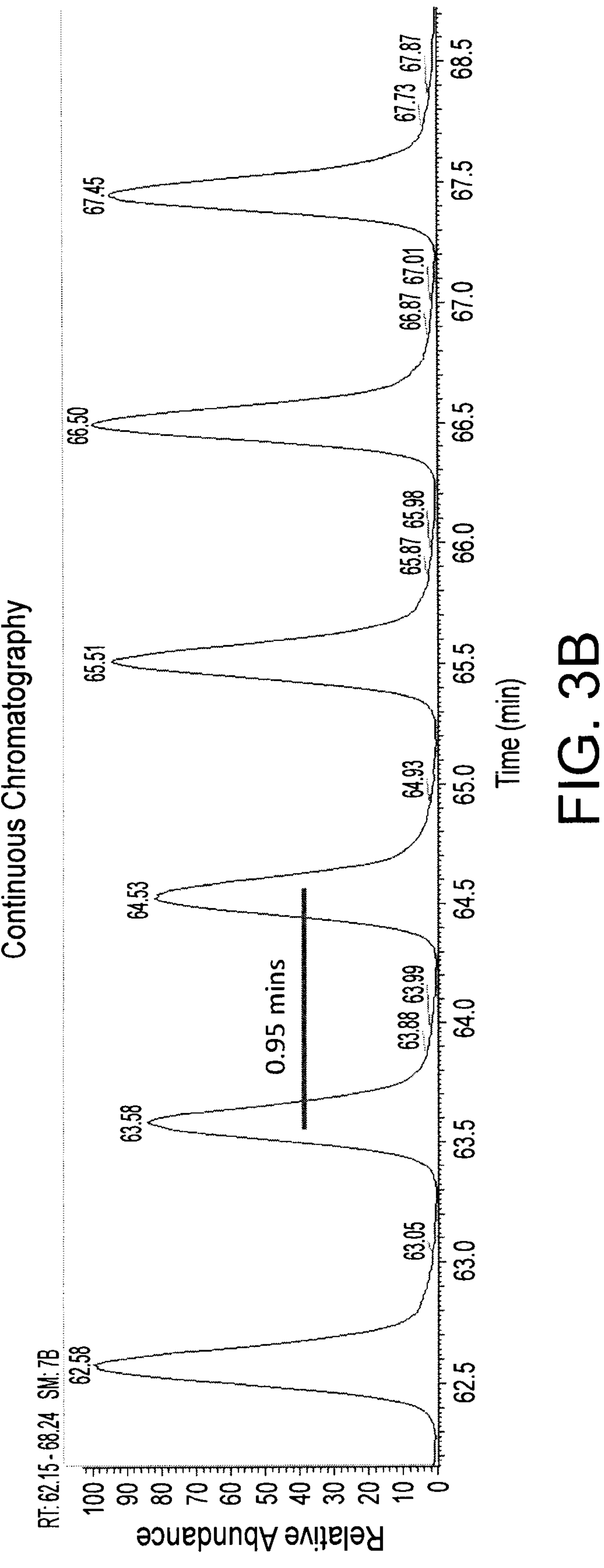

To increase sample throughput without requiring additional sample purification procedures, it is desirable to shorten the time for chromatographic separation of molecules. In one embodiment, the invention provides increasing the sample throughput by shortening the run time for sample detection by serially injecting a plurality of samples into a continuous flow of solvent through an LC system. This is known as isocratic chromatography. In this embodiment, samples may be analysed using mobile-phase chromatographic solvents that are maintained at a substantially constant composition over time (FIG. 2B). Thus, a plurality of samples can be injected onto a column without substantially altering the mobile phase solution conditions and without employing a gradient of solvents. To enable separation of the target analyte, the composition of the mobile phase is selected to enable a moderate exchange rate between bound and unbound states of the analyte. The constant composition of the solvent allows for the preferential retention of the target analyte. When the mobile phase conditions are properly adjusted, non-target analytes will remain bound to the stationary phase of the column or will be rapidly eluted from the column whereas the target molecule will be retained for a period of time sufficient to achieve separation between the target and non-target molecules. Since this strategy results in the consistent gradual migration of the target analyte through the column, a plurality of samples can be injected into a single gradient and the target analyte from each sample will elute in a time-resolved plurality of peaks whose order matches the sample injection order (FIG. 3B). Eventually, the column will require a reconditioning step, where a new solvent composition is used selected to elute and thereby clean bound moieties from the column.

Isocratic continuous elution is surprisingly useful for identifying the presence of the target compounds and analyzing complex biological samples, for example urine samples. Isocratic continuous LC allows sample-to-sample intervals of about 1 minute. The time interval between samples is affected by the column physical dimensions, the flow rate of the solvent, the chemical properties of the solvent, the chemical composition of the column stationary phase, the temperature of the column, the fluid pressure within the column, and the operational capabilities of the auto sampler (for example, the rate at which the instrumentation can perform repeat injections). Under typical analytical conditions, the time interval between eluting peaks from the target analytes will range from 30 to 90 seconds. This is a fraction of the time required for conventional gradient chromatography, as shown by comparison of FIGS. 3A and 3B.

Molecules eluting from the chromatographic setup are analyzed by spectrometry such as by NMR, mass spectrometry, UV-Vis, arrayed diode, etc. In one embodiment, liquid chromatography (LC) may be used in combination with mass spectrometry (MS). The combination LC-MS is a powerful tool used in medical sample analysis.

Figure 4:
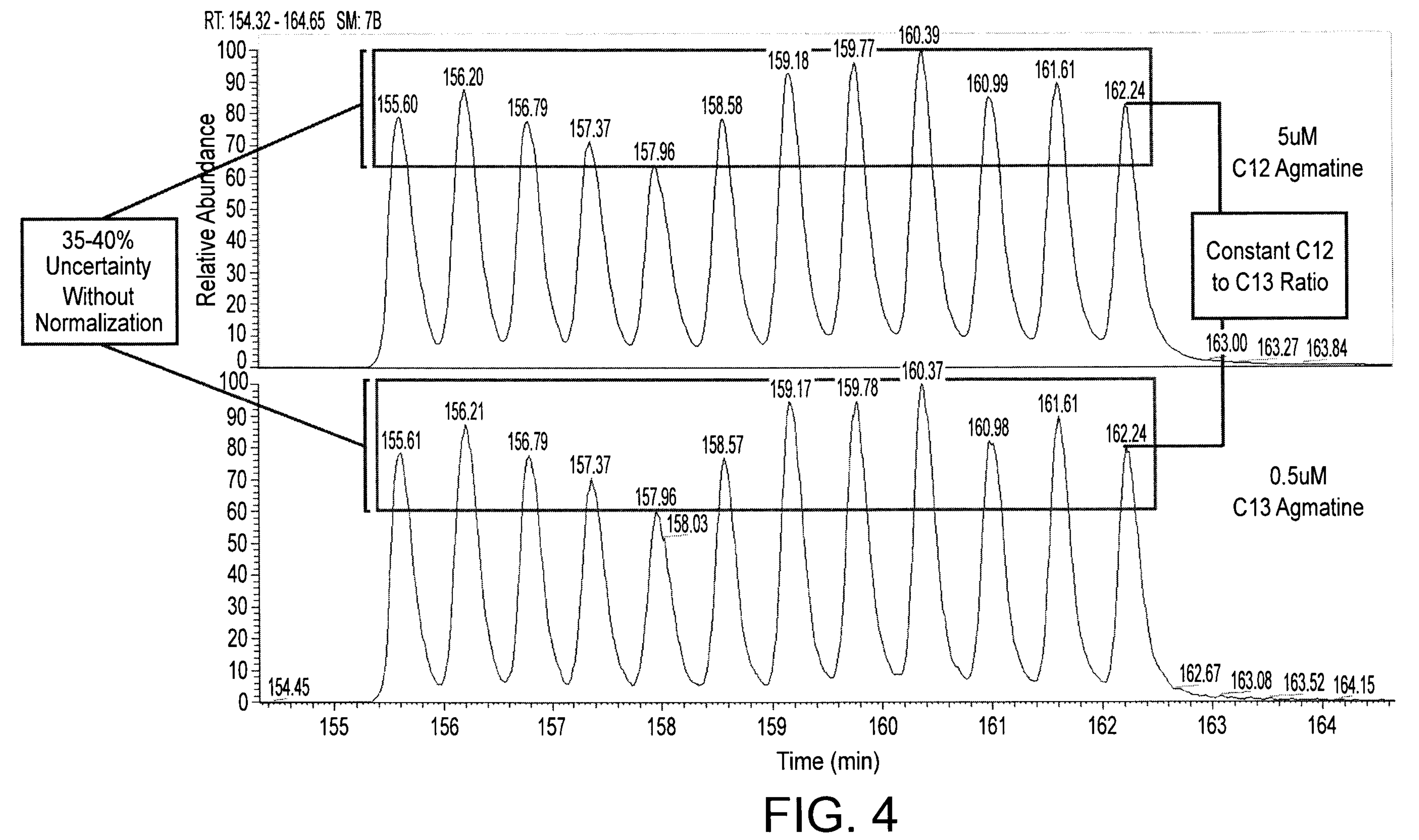
FIG. 4 is a representation of the error effect caused by differential ion suppression during isocratic continuous chromatography sample runs (upper chart) and isocratic continuous chromatography sample runs using isotope-labelled agmatine C13 (lower chart), which shows that the ratio of agmatine to isotope-labelled agmatine can be employed to correct the error.

As is illustrated in FIG. 4, an inherent problem encountered when analyzing complex samples by LC-MS is that there may be differential ion suppression where different compounds, such as salt forms, elute from the column at different rates into the detector. Differential ion suppression refers to signal variation as a result of competition for ionization of analytes within the ion source. Differential ion suppression causes even the exact same sample to show up at different intensities when injected multiple times thereby limiting the accuracy and precision of LC-MS. In FIG. 4, for example, while twelve identical aliquots of a sample containing 5 uM $^{12}C$ agmatine and 0.5 uM $^{13}C$ agmatine (isotopically labelled) were successively injected to a column running an isocratic flow of solvent, the resulting MS signals varied 35-40%. In addition to affecting signal intensities, differential retention of interfering compounds can alter chromatographic peak shape and retention time of the target analyte. These quantitative and qualitative changes in chromatographic and ionization properties are substantially unaffected when compounds contain stable isotopes of carbon ($^{13}C$) or nitrogen ($^{15}N$). To control for variations in ionization and chromatographic properties, the present invention may employ isotope-labelled target compounds agmatine, putrescine or cadaverine, which allows for accurate and reliable detection of target compounds.

Figure 5:
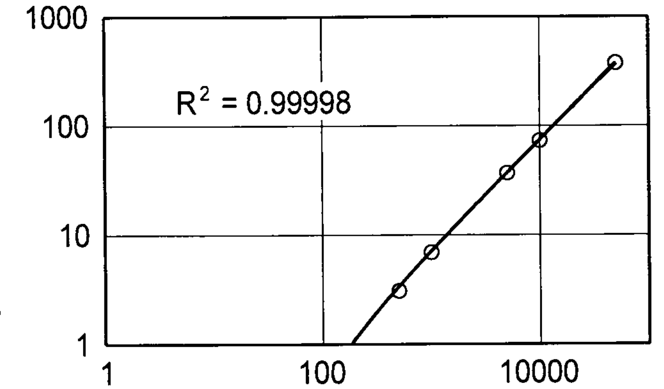
FIG. 5 shows two graphs demonstrating that accurate measurement of agmatine can be achieved by isotope-labelled agmatine over clinically relevant agmatine concentrations using isocratic continuous chromatography, isotope-labeled agmatine is added as an internal reference for each sample and concentrations are calculated by ratio of agmatine to isotope-labelled agmatine. The upper chart shows a calibration curve of $^{12}C$ agmatine standards added to urine samples containing 100 nM $^{13}C$ agmatine. The lower chart shows independent quality-control urine samples with a known amount of $^{12}C$ agmatine versus the agmatine concentrations calculated based on the observed isotopic ratio.
Figure 5:
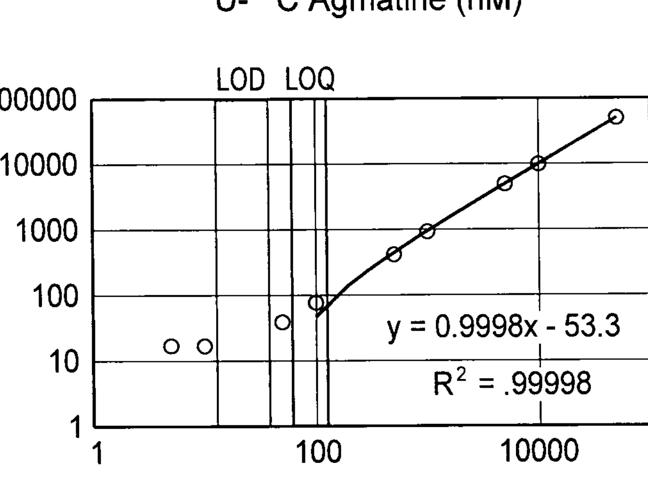

In one embodiment, therefore, isocratic continuous chromatographic elution is combined with a method in which a known concentration of an isotope-labeled version of the target analyte is added to each sample and concentrations of the target analyte are calculated from the observed ratio of $^{12}C/^{13}C$ signals. This isotope normalization strategy, also called isotope dilution, corrects for errors resulting from differential ion suppression because the target analyte and isotope-labeled target analyte co-elute and are thereby subjected to the same ionization and chromatographic conditions. As shown in FIG. 4, for example, the ratio of signal intensities for successive analyses of 5 uM $^{12}C$ agmatine to 0.5 uM $^{13}C$ agmatine remained substantially consistent in each sample even though there was signal to signal variation for the same sample. Despite the variable ion suppression inherent to LC-MS, FIG. 5 shows quantification of known concentrations of $^{12}C$ agmatine using this isotope normalization method and demonstrates that robust quantification of target analyte levels can be achieved across a wide range of concentration values, including clinically relevant concentration values. In this example, the quantitative performance of the method was assessed using a panel of healthy urine samples that were spiked with a range of $^{12}C$ agmatine standards and 100 nM U-$^{13}C$ agmatine as an internal reference. Injected samples were analysed by a column running isocratically and concentrations were calculated using a calibration curve shown in FIG. 5. The quantitative performance was assessed using an independent set of quality control samples.

Analysis of a urine sample can be spiked with a known concentration of an isotope of the target analyte, which in the case of the present method for detecting UTIs is one or more of agmatine, putrescine or cadaverine, and the signal intensity for the known concentration of isotope labelled target analyte can be employed to normalize quantitative variability and calculate the concentration of the target analyte. This method includes detecting both the target analyte and the simultaneously eluting isotope-labelled version of the target analyte and comparing their peak intensities. Using isocratic continuous elution and isotope dilution, the samples can be accurately analysed despite variability in ion suppression. This isotope dilution strategy enables target analytes to be accurately quantified in a plurality of urine samples injected sequentially into a continuous isocratic gradient.

Figures 2C, 2D:
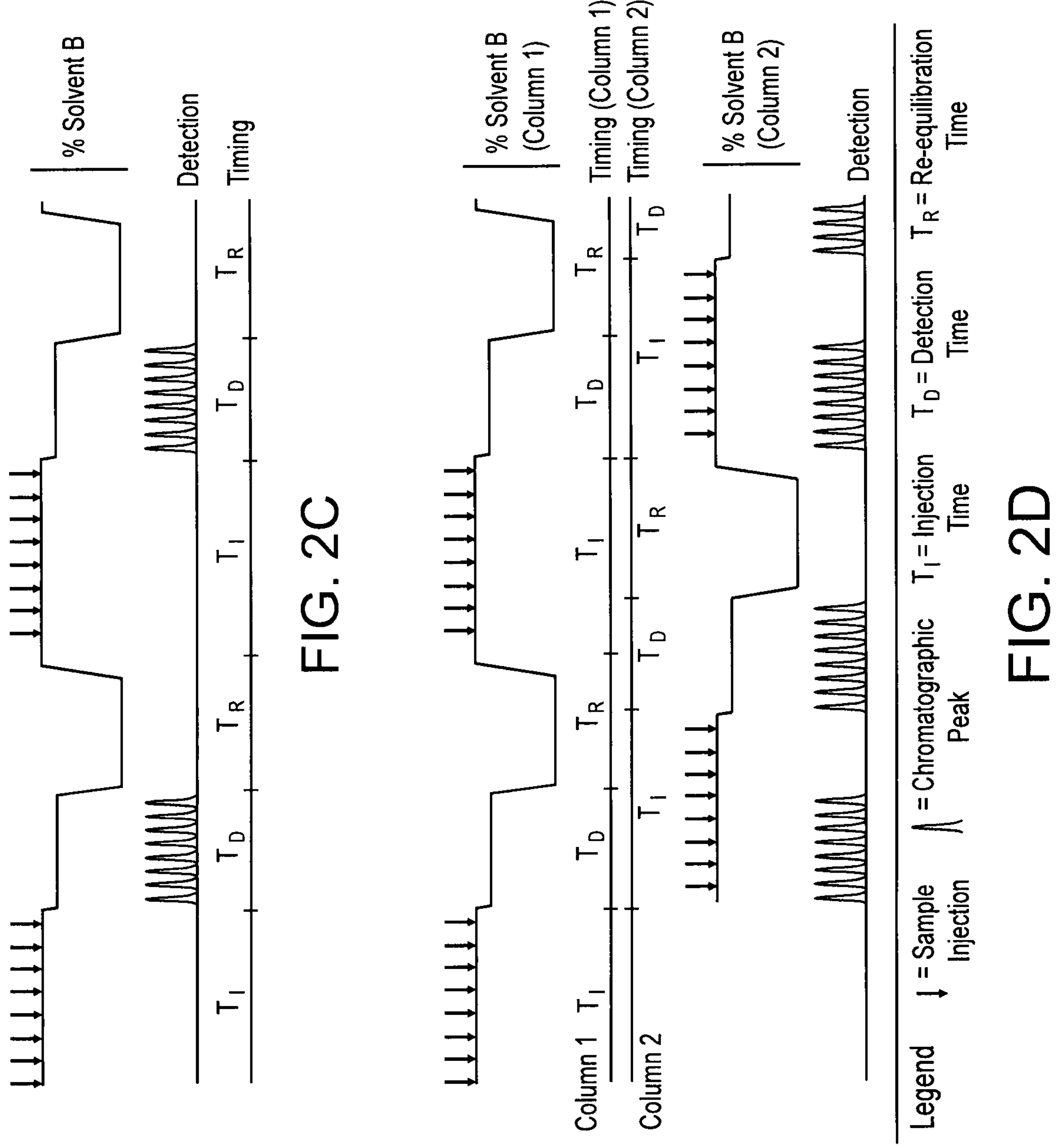

In another embodiment, chromatographic separation of analytes may include a two-stage, isocratic continuous elution to achieve good separation and close spacing of chromatographic peaks. This methodology is illustrated in FIG. 2C. For example, with reference to FIG. 2C, the two-stage isocratic continuous chromatography method comprises: in the first stage, a first mobile phase is used to inject a plurality of samples onto the column followed by a second stage, where a second mobile phase is used to elute analytes off the column for analyte detection such as by MS. The second mobile phase has a composition different from the first mobile phase. The mobile phases may differ in hydrophobicity, solvent ionic strength, solvent composition, pH, etc. depending on the type of sample, the characteristics of the target compound, and the chemical and physical properties of the column's stationary phase. In the case of agmatine, the first mobile phase differs from the second mobile phase in terms of its hydrophobicity, where the first mobile phase is more hydrophobic than the second mobile phase. The first mobile phase is selected to provide a slow elution of the target analyte off the LC column. Thus, when samples are loaded onto the column, during the first stage, using the first mobile phase, the target analyte is substantially retained on the LC column. Once loaded, the second mobile phase allows for accelerated elution of the target analyte.

Two-stage isocratic chromatography enables analysis of target analytes from a plurality of samples by enabling multiple samples to be loaded onto a column in the first stage, then rapidly eluted during the second stage. The elution of all the samples in the second stage can occur in less, sometimes much less, time than the time taken for the sample injections in the first stage. The first mobile phase is selected for the target analyte to allow moderate binding of the analyte onto the column stationary phase such that analytes from a plurality of samples migrate through the column in a progressive series of peaks. The second mobile phase is selected to elute samples off the column rapidly, but substantially maintain the binding of non-target analytes. This two-stage strategy separates the target molecule in a plurality of samples while minimizing the amount of time necessary clear the column of target analytes. The second mobile phase enables analytes from a consecutive series of samples to be eluted in a much shorter time than is possible from a single stage of chromatography. Consequently, quantitative analysis of a series of samples loaded onto a column may be completed in a fraction of the time necessary to load the samples.

To maintain fast chromatographic separation of target analytes over large number of samples, the two-stage isocratic continuous chromatography method can further include a multiplexed column injection schedule where a plurality of columns are employed (FIGS. 1 and 2D). Each column can accept a number of samples that can be sequentially loaded until the column reaches its carrying capacity. This capacity is dictated by the physical and chemical properties of the column (e.g. 12 samples for the column used for FIG. 8). Any potential timesavings through two-stage isocratic chromatography are restricted to analyses of samples in batches equal to or smaller than the carrying capacity of the column. However, multiplexing a plurality of columns allows timesavings to be extended to greater numbers of samples by sequentially loading, then eluting, target analytes off of a series of columns. Moreover, an apparatus enabling loading of multiple columns while simultaneously eluting another column could enable continuous analysis of large numbers of samples.

Figure 3C:
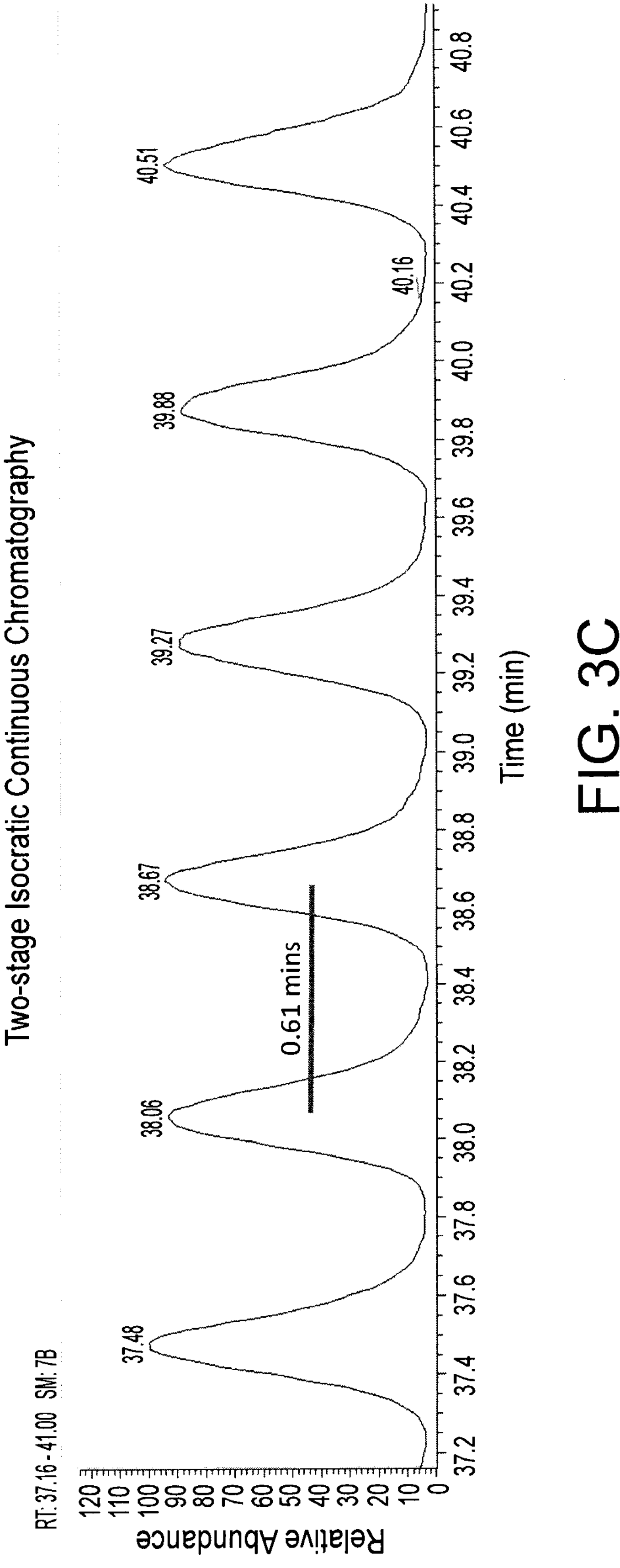

For example, as shown in FIG. 1, a LC system may including two or more columns 10*a*, 10*b*, configured to connect to the same detector, such as a mass spectrometer 12. This provides serial elution of samples off the plurality of columns 10*a*, 10*b* resulting in a substantially steady and high frequency flow of analytes entering the mass spectrometer for detection and analysis (FIG. 3C). The columns may receive samples from the same source, for example, an auto-sampler 14 with samples a first mobile phase (dashed line). Both columns 10*a*, 10*b* may also receive a second mobile phase (dotted line) from another source, for example an elution pump 16. A valve switch 18*a* may be used to switch communication between the sampler and each of the two columns while communication is also switched between the elution pump and the two columns. Another valve switch 18*b* may be provided at the output ends of the columns alternate communication of the detector to each of the first and second columns in turn. The valve switch directs eluting phases appropriately to either the mass spectrometer 12 or to waste 20. The mobile phase coming off the column may be directed to waste during re-conditioning/equilibrium stages and any time the eluting mobile phase does not need to be analyzed by the detector. If a further mobile phase is required for reconditioning, a further supply may be added to and upstream of the valve switch 18*a*.

In operation, first column 10*a* may be injected with multiple samples using the first mobile phase, while a second column may elute analytes from the sample using a second mobile phase. Blocks of samples are injected on each column at different times. The basic premise of this aspect of the method is that a series of samples are injected onto the first column and then samples are eluted off the second column, where the injection and elution occurs in an alternating or sequential fashion on separate columns. In other words, the first column is in the first stage while the second column is in the second stage. This process is cycled, while one column elutes samples into the mass spectrometer, the other re-equilibrates and is loaded up with samples, for example by an auto-sampler. There many be a plurality of columns in the first stage, where blocks of samples are injected continuously onto the columns. There may be a plurality of columns in the second stage, where the samples are rapidly eluted off the columns. Thus, in a method according to the present invention, analysing includes a two-stage, isocratic continuous elution and a multiplexed column injection schedule. This achieves high sample throughput and good use of laboratory time and resources on an LC-MS platform for targeted compound detection in complex samples.

In the possible multiplexed column injection hardware set up as shown in FIG. 1, valve switch 18*a* may be used to switch the mobile phase being run on a column rapidly between two mobile phases: first mobile phase (dashed line) having a composition selected to be suitable for injection of samples, as from the auto-sampler; and second mobile phase (dotted line) configured to rapidly elute the target compound from the column, as from elution pump 16. In FIG. 1, State A shows Column 1 in the first stage and Column 2 in the second stage; and State B, which has been switched over by the valve switch 18*a*, shows Column 1 is in the second stage and Column 2 in first stage. Valve switch 18*b* at the eluted end of the columns alternately communicates eluted analytes from the two columns one at a time to the mass spectrometer. While two columns are shown in FIG. 1, it is to be understood that this method can employ more than two columns.

While the methods of chromatography have use apart from the methods for diagnosis of a UTI, the combination offers very high throughput of samples, as is particularly useful in medical laboratories. Consider that conventional gradient methods achieve an elution time peak to peak of about 2-4 minutes, an isocratic continuous system can usually achieve an elution time peak to peak of about 0.5-1.5 minutes, and a 2-stage, isocratic system can achieve an elution time peak to peak of less than one minute such as about 0.25-1 minute (FIGS. 3A to 3C). A multiplexed 2-stage system has overall even higher throughput since two or more columns can be accepting samples at the same time and feeding to one detector. Therefore, in another embodiment, isocratic continuous chromatography is used to detect the presence of at least one decarboxylated amino acid metabolite selected from agmatine, putrescine or cadaverine for diagnosing a patient suffering from a UTI, wherein culture-independent urine sample from the patient is analyzed by isocratic continuous chromatography. In another embodiment two-stage, isocratic continuous chromatography is used to detect the presence at least one decarboxylated amino acid metabolite selected from agmatine, putrescine or cadaverine for use in diagnosing a patient suffering from a UTI, wherein culture-independent urine samples from the patient is analyzed by two-stage, isocratic continuous chromatography. In another embodiment a multiplexed column injection schedule where a plurality of columns are employed and a two-stage, isocratic continuous chromatography is used to detect the presence at least one decarboxylated amino acid metabolite selected from agmatine, putrescine or cadaverine for use in diagnosing a patient suffering from a UTI, wherein culture-independent urine sample from the patients is analyzed by two-stage, isocratic continuous chromatography.

In another embodiment, analyzing a urine sample from the patient is achieved using LC-MS focusing on detection of agmatine. Agmatine has shown the highest level of ionization and highest predictive capacity relative to putrescine and cadaverine.

Again, while a method is described for analysis of UTIs and specifically with respect to target analytes agmatine, putrescine or cadaverine, it is to be understood that the methods for LC described herein are useful for other applications for targeted compound detection in samples.

EXAMPLES

Example IA—Analysis of Urine Samples Using Isocratic Continuous Chromatography A method for continuous isocratic chromatography was initially optimized using simulated UTI samples constructed from an unlabeled agmatine standard spiked into a healthy urine control sample. Optimal isocratic solvent composition for agmatine was determined to be 86% acetonitrile with 0.1% (v/v) formic acid, which allowed for high binding while still maintaining mobility of agmatine on the column to allow for quick plug spacing. An offset between binding and elution of about 4% was deemed beneficial to improve the chromatographic peak shape while expediting column elution and maintaining baseline separation between sample peaks, as shown in FIG. 3B. These conditions enabled serial injection with as little as 30 second spacing between peaks. Once optimal solvent ratio was determine, urine samples were injected with isotope-labelled $^{13}$C agmatine.

Example IB—Analysis of Isotope Diluted, Two-Stage, Isocratic Continuous Elution and with a Multiplexed Column Injection Urine samples were spiked with $^{13}$C agmatine and analyzed on a Thermo Q-Exactive™ HF LC-MS platform using a Syncronis™ HILIC column. A binary solvent system comprising 20 mM ammonium formate pH 3.00 (solvent A) and acetonitrile with 0.1% (v/v) formic acid (solvent B) was employed for chromatographic separation. Mass spectra were collected in positive ion mode using parallel reaction monitoring. Isotope diluted, two-stage, isocratic continuous elution with a multiplexed column injection schedule analyses were conducted by i) serially injecting isotope-tagged urine samples in a continuous 86% solvent B (first mobile phase) isocratic flow and ii) eluting the serial sample plugs using an isocratic step at 82% solvent B (second mobile phase). Hardware including a switch valve (FIG. 1) ensured that step i) was conducted in the first column while step ii) was conducted in the second column and that the solvent was immediately changed when changing the elution from first mobile phase to second mobile phase and back to the first mobile phase, in an alternating fashion. Differential ion suppression was controlled by quantifying the isotope ratio between native agmatine metabolites versus the co-eluting $^{13}$C standards.

Example 1C—Error Correction as Shown in FIG. 4

A sample of urine spiked with 5 uM $^{12}$C and 500 nm U-$^{13}$C agmatine is injected 12 times in a row using isocratic continuous chromatography. Note how the signal errors (illustrated by signal to signal variance) for both the target compound, specifically agmatine and the isotope-labelled agmatine are the same for each sample. Thus, computing the concentration of the $^{12}$C analyte from the observed ratio of $^{12}$C versus $^{13}$C signals cancels out error term, for example differential ion suppression, which may be caused by variations in ionization or chromatography sample-to-sample. This method enables the concentrations of analytes to be accurately determined despite significant sample-to-sample and column-to-column variability in the performance of the detection system.

Figure 6:
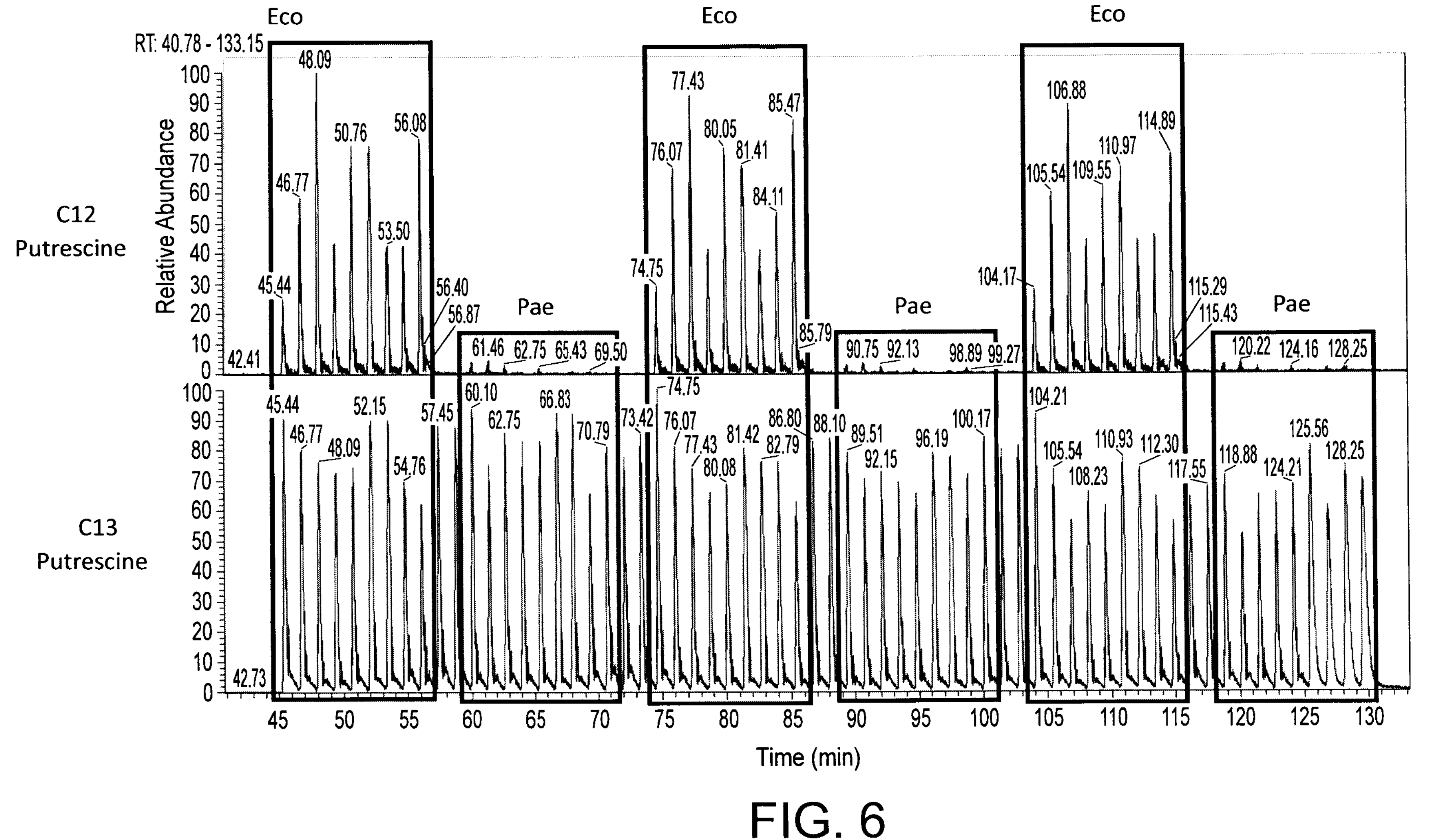
FIG. 6 is a comparison of the levels of $^{12}C$ and $^{13}C$ putrescine in nine *Escherichia coli* cultures and nine *Pseudomonas aeruginosa* cultures analyzed by isocratic continuous chromatography (3 technical replicates). The culture methods used to generate these samples are compatible with the established methods for detecting bloodstream infections.

Example 2—Blood Culture Diagnosis as Shown in FIG. 6

While shown above for urine analysis, the present method is also applicable for other systems. For example, as shown in FIG. 6, two-stage, isocratic continuous chromatography was used to distinguish nine microbial cultures of *P. aeruginosa* (Pae) from *Escherichia coli* (Eco). *P. aeruginosa* does not produce putrescine whereas *Escherichia coli* produces significant levels of putrescine under the microbial culture conditions used for this assay. Consequently, cultures growing *Escherichia coli* could be differentiated from cultures growing *P. aeruginosa* on the basis of putrescine levels observed in the samples. As shown in FIG. 6, there are nine peaks detected, representing the nine urine samples and three blocks of peaks eluting over time, representing three technical replications that were performed demonstrating the stability and reliability of the method. The microbial culture example used here illustrates the general applicability of the method for microbial analyses. Moreover, the microbial culture conditions used for this study are similar to those used in analysis of bloodstream infections (BSIs) and thereby indicate the applicability of the method to other clinical applications, including detection of BSIs.

Figure 7:
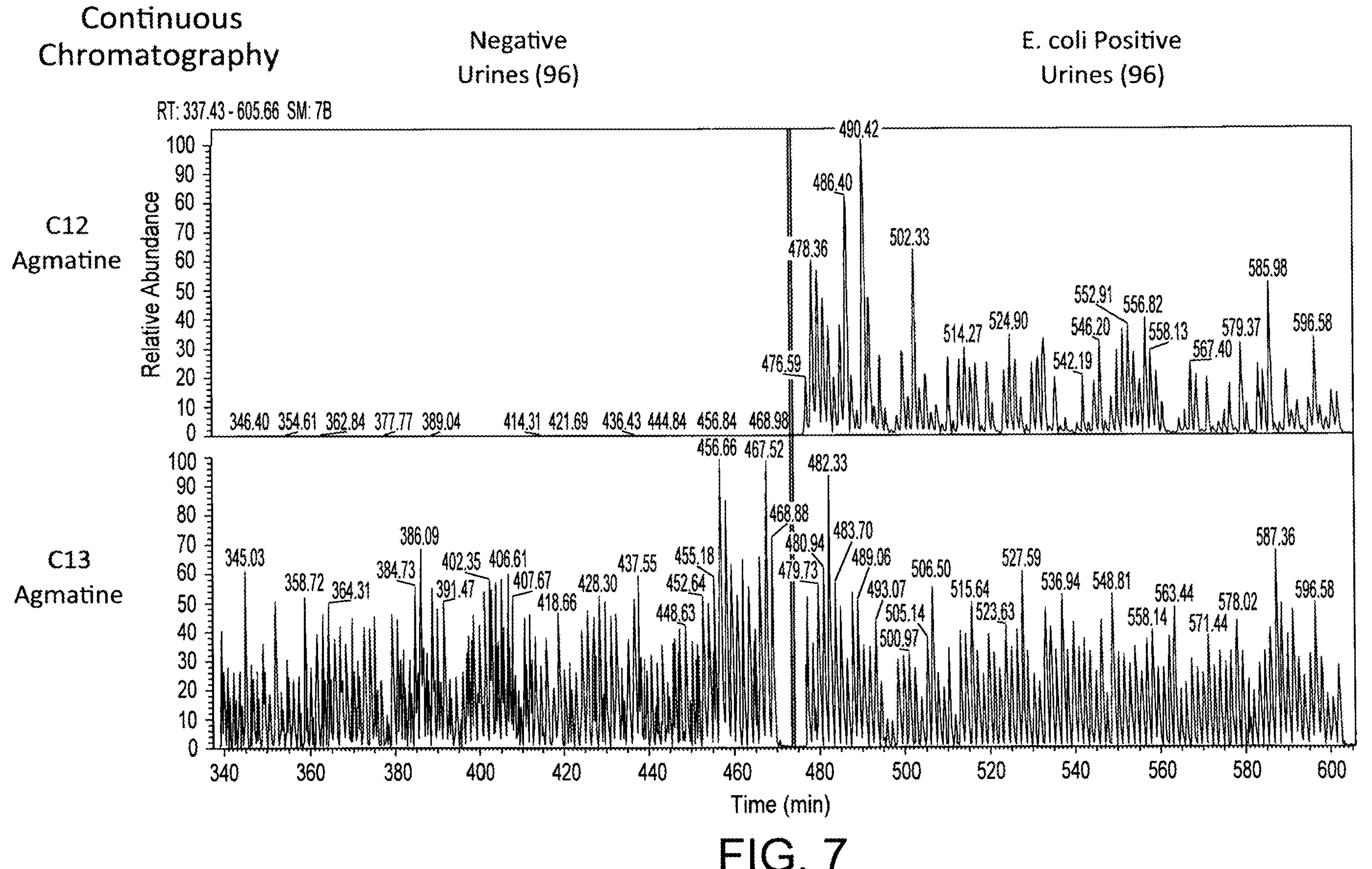
FIG. 7 is a comparison of the levels of $^{12}C$ and $^{13}C$ agmatine levels in ninety-six human urine samples that tested negative for bacterial growth using isocratic continuous chromatography (upper left chart) versus ninety-six human urine samples that tested positive for *Escherichia coli* infection using isocratic continuous chromatography (upper right chart). Concentrations of $^{12}C$ agmatine were calculated from the ratio of $^{12}C/^{13}C$ multiplied by the known concentration of the $^{13}C$ agmatine standard (lower chart showing isotopically labelled agmatine standard).
Figure 8:
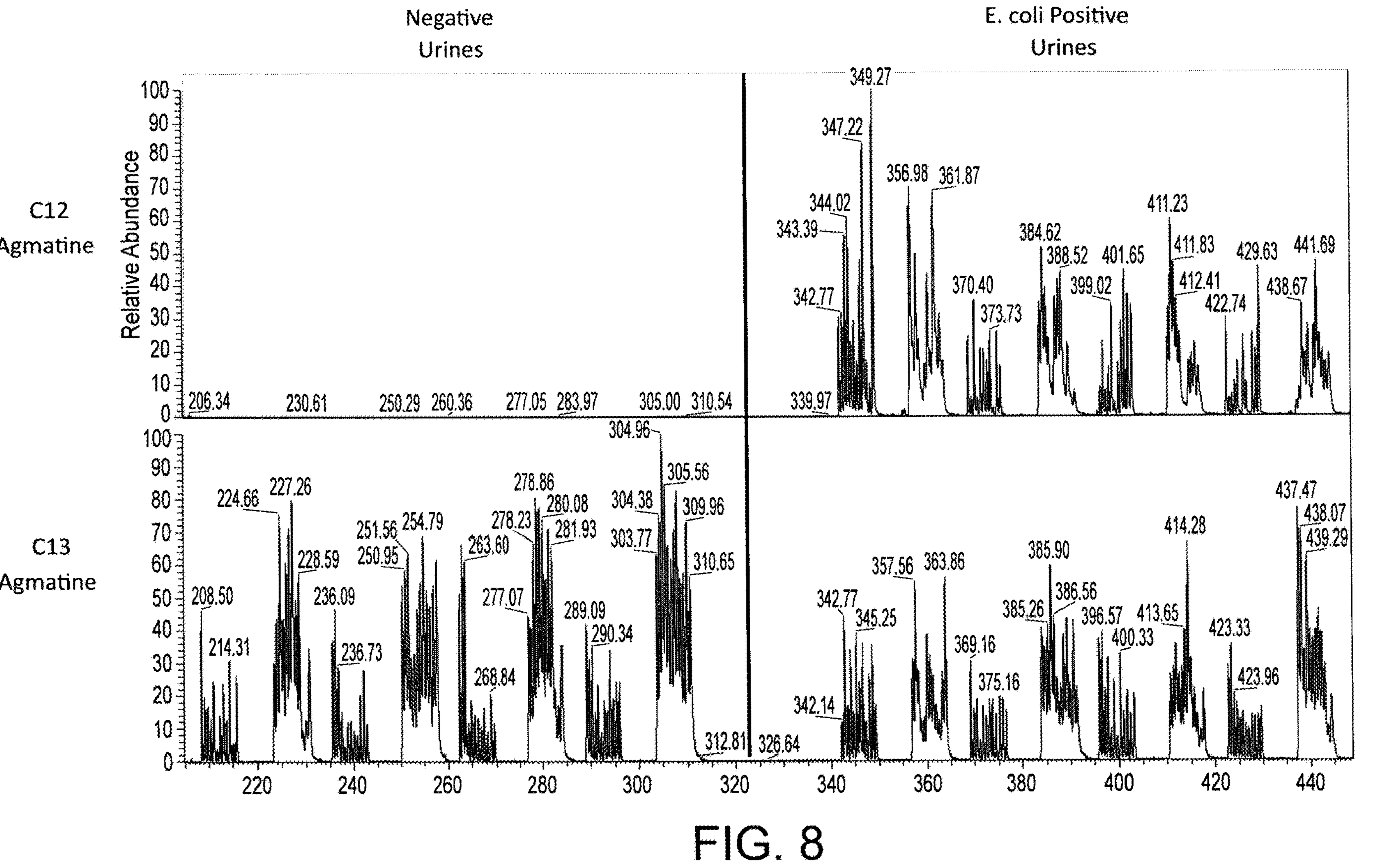
FIG. 8 is a comparison of the levels of $^{12}C$ and $^{13}C$ agmatine of ninety-six human urine samples that tested negative for bacterial growth using two-stage, isocratic continuous chromatography with a multiplexed column injection schedule where two columns were employed (upper left chart) versus ninety-six human urine samples that tested positive for *Escherichia coli* infection using two-stage, isocratic continuous chromatography with a multiplexed column injection schedule where two columns were employed (upper right chart). Concentrations of $^{12}C$ agmatine were calculated from the ratio of $^{12}C/^{13}C$ multiplied by the known concentration of the $^{13}C$ agmatine standard (lower chart showing isotopically labelled agmatine standard).

Example 3—UTI Detection—FIGS. 7 and 8

Following optimization, a cohort of ninety-six urine samples from patients with and without urinary tract infections (UTIs) were analyzed under two conditions: i) Example IA, namely isotope-labelled, isocratic continuous chromatography (FIG. 7); and ii) Example IB, namely isotope-labelled, two-stage, isocratic continuous chromatography with a multiplexed column injection schedule (FIG. 8). This study produced promising results. The method of quantification by isotope ratio achieved error rates comparable to those observed in more traditional 15 minute linear gradients.

In particular, a set of ninety-six urine samples from patients suffering from UTIs, specifically *Escherichia coli* are shown compared to ninety-six urine samples from healthy patients. The bottom chart of FIGS. 7 and 8 shows the detection of isotope labelling of $^{13}$C agmatine, the upper left chart of FIGS. 7 and 8 shows ninety-six urine samples which tested negative for a UTI and the upper right chart of FIGS. 7 and 8 shows ninety-six urine samples which tested positive for *Escherichia coli*. In FIG. 7, the samples were analyzed by isocratic continuous chromatography according to the methodology described in Example IA and in FIG. 8, the samples were analyzed by two-stage, isocratic continuous chromatography with a multiplexed column injection schedule according to the methodology described in Example IB. Each of FIGS. 7 and 8 show negative urine samples (no infection by UTI-causing microorganisms) on the upper left hand chart and *Escherichia* co/i-infected urine samples on the upper right hand chart.

These data suggest that both isocratic continuous chromatography and two-stage, isocratic continuous chromatography with a multiplexed column injection schedule could provide feasible strategies for high-throughput quantitative analyses of select biomarkers. Moreover, the methods were directly applicable to the detection of UTIs.

It is noted from comparing the results from FIGS. 7 and 8 that two-stage, isocratic continuous chromatography with a multiplexed column injection schedule (FIG. 8) provides shorter run times for sample detection than isocratic continuous chromatography (FIG. 7). It was noted that using isocratic continuous chromatography a sample per minute to a sample per 30 seconds could be detected whereas the sample elution/detection times were further compressed using two-stage, isocratic continuous chromatography with a multiplexed column injection schedule.

Example 4—Blinded Clinical Study

In order to validate the methods of the invention, a blinded cohort of urine samples from patients were subjected to two-stage, isocratic continuous chromatography with a multiplexed column injection schedule to detect native agmatine content. The patient urine samples were separately analyzed via traditional UTI diagnostic methods. Using only agmatine, the data suggests that agmatine presence in uncultured or culture-independent urine samples can diagnose roughly 85% of patients that present clinically with a bacterial urinary tract infection. In this study, 192 patient samples were submitted to multicolumn, two-stage and isocratic continuous chromatography analysis as in Example IB. The overall run time was 430 minutes, which included 192 patient samples with two technical replicates and a number of quality control blank injections providing 448 total injections. This averages out to an average run time of 1.1 minutes per patient sample overall and 0.96 minutes per injection. Of the 192 patient samples, only one false positive was observed. The false positive was likely a product of differences between the internal positivity threshold and that of the traditional microbiology assay. All false negatives were expected, coming from microbes that are not known to produce agmatine in urine. Overall this is an extremely fast and effective screen compared to conventional detection methodologies that if implemented would have a significant impact on the speed of diagnosis of UTIs as well as circumvent the need to culture 85% of patient samples. Only the negative samples would have to be cultured for confirmation of bacterial UTI.

Example 5—Urine and Boric Acid Experiment

Urine samples are typically collected in urine culture tubes containing a buffered boric acid solution that minimizes microbial growth during sample transport to the microbiology laboratory. To assess the impact of growth preservatives on agmatine production, seven strains of *Escherichia coli* (MG1665, ATCC 25922, ESBL ATCC BAA-196, and 4 clinical isolates) were seeded in Mueller Hinton medium overnight, and subcultured in filter-sterilized urine with or without preservatives (boric acid, 2.63 mg/mL; sodium borate, 3.95 mg/mL; sodium formate, 1.65 mg/mL). Bacterial samples were seeded at 105 CFU/mL in respective medium in a 96-well plate and incubated statically at 37° C. in the presence of 5% $CO_2$. Growth was monitored ($OD_{600\ nm}$) using a Microskan GO plate reader (Thermo Scientific, Waltham, MA). Samples for MS were first centrifuged (4200 g, 10 min, at 4° C.) to pellet out microbes. Supernatant was then diluted 1:1 in MeOH, and stored at −20° C. Samples were thawed, and immediately re-centrifuged (4200 g, 10 min, at 4° C.) to precipitate out any residual proteins, and diluted in 50% MeOH to a final dilution of 1:20. Samples were analyzed on a Q Exactive™ HF Mass Spectrometer (Thermo Scientific, Waltham, MA). LC-MS analysis showed that the concentration of agmatine in the sample was effectively the same after the incubation time with the preservative as it was immediately before contact with the preservative; no significant microbial growth or agmatine production were detected over this incubation in samples containing a boric acid preservative solution whereas significant growth and agmatine production were observed in samples that did not include the preservative. Consequently, it was found that the boric acid preservative solution substantially inhibited both microbial growth and agmatine production over sample storage timelines consistent with clinical practice. It was determined that standard urine sample collection in a boric acid tube would not influence agmatine concentration in the sample.

Example 6—Metabolic Preference Assay

A cohort of *Escherichia coli* positive urine samples with a diverse range of susceptibility profiles were analyzed by metabolic preference assay. Bacteria from these samples were pelleted, washed, and re-suspended in equal volumes of Mueller Hinton medium. 96-well plates were seeded with 10% of the washed cells, were incubated for four hours in the presence or absence (No AB) of clinically relevant concentrations of antibiotics, and were analyzed by LC-MS (FIG. 10). Metabolic preference assay based diagnostics closely recapitulated the antibiotic susceptibility profiles reported via the traditional culture-based approach. There was substantial agreement between the breakpoints determined by metabolic preference assay based and traditional culture-based approaches for the antibiotics. The metabolic preference assay strategy correctly assigned antibiotic susceptibilities in 97% of samples.

Example 7—Agmatine as an Indicator of a UTI

To assess the performance of agmatine as a predictor of UTIs, a data set of 519 urine samples obtained from Alberta Public Laboratories was analyzed. This data revealed that native agmatine concentrations were tightly linked to culture positive samples containing Enterobacteriaceae (FIG. 11). All 11 Enterobacteriaceae species (ENT) observed in the data set produced agmatine at a median concentration of 2.1 μM, whereas no detectable agmatine was present in the culture-negative samples or those classified as doubtful clinical significance by Alberta Public Laboratories (FIG. 11). Although a large percentage of UTIs are caused by Enterobacteriaceae, a small proportion of UTIs result from other microbes. The data set included a limited number of these organisms (Non-ENT), none of which produced detectable levels of agmatine. Using the data set, a diagnostic agmatine threshold of about 0.17 μM for differentiating culture-negative versus culture-positive samples was calculated. This threshold was calibrated to correspond to about 97% specificity and 94% sensitivity for the detection of Enterobacteriaceae-linked UTIs.

Example 8—Solid Phase Extraction (SPE) of Agmatine from Urine Samples

Urine samples in 50% methanol (1.2 mL) were centrifuged at 14,800 g for five minutes. From these samples, 800 μL of urine was added to 200 μL isotope-dilution solution of 1 μM [U-13C] agmatine and 100 mM ammonium bicarbonate (pH 8.0) in 50% methanol for a final concentration of 200 nM [U-13C] agmatine and 20 mM ammonium bicarbonate. Thermo Scientific HyperSep Silica 96-well plates (25 mg bed volume, 1 mL column capacity) were pre-equilibrated with 400 μL HPLC-grade methanol followed by 400 μL 50% HPLC-grade methanol/H2O. Following equilibration, the 1 mL prepared sample was added to the column and allowed to drip through. Next, a methanol wash was conducted with 1 mL HPLC methanol followed by a water wash with 1 mL HPLC water. All of the solutions used in the washing steps were assisted through the columns by centrifugal force (20 g for 5 min). The column was then primed by adding 250 μL of 99.9% methanol with 0.1% formic acid. To elute the molecules of interest, 125 μL H2O with 2% formic acid was allowed to drip through the column. Ammonium bicarbonate (pH=8.0) was added to a final concentration of 100 mM in order to raise the solution to a pH >3.0 prior to LC-MS/MS analysis. Note: the first set of 196 samples contained a 13C agmatine concentration of 100 nM and a final volume of 500 μL.

The previous description and examples are to enable the person of skill to better understand the invention. The invention is not be limited by the description and examples, but instead given a broad interpretation based on the claims to follow.

We claim:

1. A method of diagnosing and treating an Enterobacteriaceae-caused urinary tract infection (UTI) in a human patient suspected of having a UTI, the method comprising:
- receiving a urine sample from the patient;
- analyzing the urine sample using at least one of liquid chromatography and mass spectrometry to determine a concentration of agmatine in the urine sample;
- diagnosing the patient as having an Enterobacteriaceae-caused UTI when the concentration of agmatine detected in the urine sample is greater than 170 nM; and
- treating the Enterobacteriaceae-caused UTI with an effective amount of an antibiotic that is active against an Enterobacteriaceae species.

2. The method of claim 1, wherein analyzing further includes adding a known quantity of an isotopically labelled version of agmatine into the urine sample for determining the concentration of the agmatine.

3. The method of claim 1 wherein after diagnosing, the method further includes:
- incubating the patient's urine sample in a growth medium;
- after incubation, analyzing the incubated growth medium by chemical analysis to determine a level of each of one or more metabolites in the incubated growth medium;
- identifying a type of Enterobacteriaceae bacteria causing the UTI by comparison of the level of each of the one or more metabolites with reference metabolite profiles and matching the level of each of the one or more metabolites with a reference metabolite profile indicative of the type of Enterobacteriaceae bacteria; and
- selecting an antibiotic to be active against the type of Enterobacteriaceae bacteria.

4. The method according to claim 1, wherein the antibiotic comprises ampicillin, cefazolin, ciprofloxacin, or trimethoprim-sulfamethoxazole, or any combination thereof.

5. The method according to claim 4, further comprising a treatment comprising a cephalosporin, nitrofurantoin, fosfomycin, or a fluoroquinolone.

* * * * *